United States Patent
Brehmer et al.

(10) Patent No.: US 11,999,993 B2
(45) Date of Patent: Jun. 4, 2024

(54) USE OF BIOMARKERS IN IDENTIFYING CANCER PATIENTS THAT WILL BE RESPONSIVE TO TREATMENT WITH A PRMT5 INHIBITOR

(71) Applicant: Janssen Pharmaceutica NV, Beerse (BE)

(72) Inventors: Dirk Brehmer, Freiburg (DE); Lijs Beke, Antwerp (BE); Dana Suzanne Gaffney, Green Lane, PA (US); Christopher H. Moy, Schwenksville, PA (US)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 17/669,008

(22) Filed: Feb. 10, 2022

(65) Prior Publication Data
US 2022/0205026 A1    Jun. 30, 2022

Related U.S. Application Data

(62) Division of application No. 16/487,852, filed as application No. PCT/EP2018/054644 on Feb. 26, 2018, now Pat. No. 11,279,970.

(60) Provisional application No. 62/464,006, filed on Feb. 27, 2017.

(51) Int. Cl.
*C12Q 1/6827*    (2018.01)
*G16H 50/30*    (2018.01)

(52) U.S. Cl.
CPC .......... *C12Q 1/6827* (2013.01); *G16H 50/30* (2018.01); *C12Q 2600/106* (2013.01); *C12Q 2600/112* (2013.01); *C12Q 2600/118* (2013.01)

(58) Field of Classification Search
None
See application file for complete search history.

(56) References Cited

U.S. PATENT DOCUMENTS

| | | | |
|---|---|---|---|
| 4,224,438 | A | 9/1980 | Fauland et al. |
| 6,143,749 | A | 11/2000 | Bhagwat et al. |
| 9,856,218 | B2 | 1/2018 | Baiocchi et al. |
| 10,653,711 | B2 | 5/2020 | Wu et al. |
| 11,059,850 | B2 | 7/2021 | Verhoeven et al. |
| 2003/0225205 | A1 | 12/2003 | Epple et al. |
| 2003/0232783 | A1 | 12/2003 | Ibrahim et al. |
| 2004/0043959 | A1 | 3/2004 | Bloom et al. |
| 2005/0209176 | A1 | 9/2005 | Meutermans et al. |
| 2006/0167241 | A1 | 7/2006 | Hayakawa |
| 2008/0132525 | A1 | 6/2008 | Wahhab et al. |
| 2011/0159111 | A1 | 6/2011 | Curry et al. |
| 2012/0035115 | A1 | 2/2012 | Manoharan et al. |
| 2013/0023491 | A1 | 1/2013 | Annes et al. |
| 2013/0310333 | A1 | 11/2013 | Chesworth et al. |
| 2013/0310334 | A1 | 11/2013 | Chesworth et al. |
| 2014/0100184 | A1 | 4/2014 | Song et al. |
| 2014/0213582 | A1 | 7/2014 | Duncan et al. |
| 2014/0221345 | A1 | 8/2014 | Duncan et al. |
| 2014/0228343 | A1 | 8/2014 | Duncan et al. |
| 2014/0329794 | A1 | 11/2014 | Duncan et al. |
| 2016/0009744 | A1 | 1/2016 | Duffey et al. |
| 2016/0244475 | A1 | 8/2016 | Tatlock et al. |
| 2017/0198006 | A1 | 7/2017 | Duncan et al. |
| 2018/0243328 | A1 | 8/2018 | Wu et al. |
| 2019/0263833 | A1 | 8/2019 | Wu et al. |
| 2020/0010881 | A1 | 1/2020 | Brehmer et al. |
| 2020/0360416 | A1 | 11/2020 | Wu et al. |

FOREIGN PATENT DOCUMENTS

| | | |
|---|---|---|
| JP | 2005-527502 A | 9/2005 |
| JP | 2006-503020 A | 1/2006 |
| JP | 2016-505001 A | 2/2016 |
| TW | 200304380 A | 10/2003 |
| TW | 1730980 B | 6/2021 |
| WO | 96/40686 A1 | 12/1996 |
| WO | 03/39523 A2 | 5/2003 |
| WO | 03/70739 | 8/2003 |
| WO | 03/74083 | 9/2003 |
| WO | 2004/022572 A1 | 3/2004 |
| WO | 2005/065150 A2 | 7/2005 |
| WO | 2006/078752 A2 | 7/2006 |
| WO | 2010/039548 A2 | 4/2010 |
| WO | 2011/075665 A2 | 6/2011 |
| WO | 2012/075500 A2 | 6/2012 |
| WO | 2012/082436 A2 | 6/2012 |
| WO | 2012/083170 A1 | 6/2012 |

(Continued)

OTHER PUBLICATIONS

Ensembl record for Gene: RBM10 found online at https://useast.ensembl.org/Homo_sapiens/Gene/Variation_Gene/Table?db=core;g=ENSG00000182872;r=X:47145221-47186813 and accessed Feb. 17, 2023.*
Ensembl record for SNP rs782678696 found online at https://useast.ensembl.org/Homo_sapiens/Variation/Explore?r=X:47184692-47185692;v=rs782678696;vdb=variation;vf=131714249 and accessed Feb. 17, 2023.*
Ensembl record for SNP rs886044715 found online at https://useast.ensembl.org/Homo_sapiens/Variation/Explore?r=X:47181769-47182769;v=rs886044715;vdb=variation;vf=134523710 and accessed Feb. 17, 2023.*
HUGO Gene Nomenclature Committee (HGNC) reports for the Major Spliceosome found online at https://Awww.genenames.org/data/genegroup/#!/group/1518 and accessed Apr. 20, 2021.*
Li (Expert Opinion on Therapeutic Patents 2019 vol. 29 No. 2 pp. 97-114).*
Evans (Science 1999 vol. 286 pp. 487-491).*
Dermer (Biotechnology 1994 vol. 12 p. 320).*

(Continued)

*Primary Examiner* — Amanda Haney
(74) *Attorney, Agent, or Firm* — BakerHostetler

(57) ABSTRACT

The present disclosure describes methods of identifying a patient that is likely to be responsive to treatment with a protein arginine N-methyltransferase 5 (PRMT5) inhibitor. The methods include evaluating a biological sample from the patient for the presence of a spliceosome mutation or alteration, wherein the presence of the alteration indicates a higher likelihood for the patient to be responsive to treatment with the PRMT5 inhibitor than in the absence of the mutation or alteration.

8 Claims, No Drawings

(56) References Cited

FOREIGN PATENT DOCUMENTS

| WO | 2012/138530 A1 | 10/2012 |
|---|---|---|
| WO | 2013/062943 A1 | 5/2013 |
| WO | 2013/151975 A1 | 10/2013 |
| WO | 2014/035140 A2 | 3/2014 |
| WO | 2014/100695 A1 | 6/2014 |
| WO | 2014/100719 A2 | 6/2014 |
| WO | 2014/100730 A1 | 6/2014 |
| WO | 2015/106025 A1 | 7/2015 |
| WO | 2015/200680 A2 | 12/2015 |
| WO | 2016/135582 A1 | 9/2016 |
| WO | 2017/032840 A1 | 3/2017 |
| WO | 2017/153186 A1 | 9/2017 |
| WO | 2018/065365 A1 | 4/2018 |
| WO | 2018/154104 A1 | 8/2018 |

OTHER PUBLICATIONS

Welliver (International Journal of Radiation Oncology Biology Physics vol. 87 Issue 2 Supplement S656 Oct. 1, 2013).*
A.J.Herrera et al., "Stereocontrolled photocyclization of 1,2-diketones: application of a 1,3-acetyl group transfer methodology to carbohydrates," Journal of Organic Chemistry, vol. 73, Mar. 28, 2008, pp. 3384-3391.
Alinari et al., "Selective inhibition of progen agrinine methyltransferase 5 blocks initiation and maintenance of B-cell transformation.", Blood, Apr. 16, 2015, pp. 2530-2543, vol. 125(16).
Andreu-Perez, P. et al., "Protein Arginine Methyltransferase 5 Regulates ERK 1/2 Signal Transduction Amplitude and Cell Fate Through CRAF", Sci. Signal, (2011), p. ra58, vol. 4, No. 190.
Antonysamy, S., et al., "Crystal structure of the human PRMT5:MEP50 complex", Proc. Natl Acad Sci, (2012), pp. 17960-17965, vol. 109, No. 44.
Barbash, O., et al., "Abstract LB-248: Protein arginine methyltransferase 5 (PRMT5) inhibition as a therapeutic strategy in B-cell lymphoma", Cancer Research, (2015), see Abstract.
Bezzi, M., et al., "Regulation of constitutive and alternative splicing by PRMT5 reveals a role for Mdm4 pre-mRNA in sensing defects in the spliceosomal machinery", Genes & Development, (2013), pp. 1903-1916, vol. 27, No. 17.
Braun, C.J., et al., "Coordinated Splicing of Regulatory Detained Intrans within Oncogenic Transcripts Creates an Exploitable Vulnerability in Malignant Glioma", Cancer Cell, (2017), pp. 411-426, vol. 32, No. 4.
Bundegaard, H., "Design of Prodrugs", Elsevier, New York-Oxford, (1985), pp. 1-92.
Chan-Penebre, E., et al., "A selective inhibitor of PRMT5 with in vivo and in vitro potency in MCL models", Nature Chemical Biology, (2015), pp. 432-437, vol. 11, No. 6.
Crane et al., Journal of Organic Chemistry, 45(19), 1980, pp. 3827-3831.
Deady, L.W., "Ring Nitrogen Oxidation of Amino Substituted Nitrogen Heterocycles with m-Chloroperbenzoic Acid", Synthetic Communications, (1977), pp. 509-514, vol. 7, No. 8.
Dermer, "Another Anniversary for the War on Cancer", Biotechnology, 1994, vol. 12, p. 320.
Devkota, K., et al., "Analogues of the Natural Product Sinefungin as Inhibitors of EHMT1 and EHMT2", ACS Med Chem Lett, (2014), pp. 293-297, vol. 5.
Di Lorenzo, A., et al., "Histone arginine methylation", FEBS Letters, (2011), pp. 2024-2031, vol. 585, No. 13.
European Search Report; EP Patent Application No. EP Patent Application No. 15184011.3; dated Oct. 22, 2015.
Evans, et al., "Pharmacogenomics: Translating Functional Genomics into Rational Therapeutics", Science, 1999, vol. 286, pp. 487-491.
Friesen, W.J., et al., "The Methylosome, a 20S Complex Containing JBP1 and pICIn, Produces Dimethylarginine-Modifiied Sm Proteins", Molecular and Cellular Biology, (2001), pp. 8289-8300, vol. 21, No. 24.

Geoghegan, V., et al., "Comprehensive identification of arginine methylation in primary T cells reveals regulatory roles in cell signaling", Nature Communications, (2015), p. 6758, vol. 6.
Graubert, et al., "Recurrent mutations in the U2AF 1 splicing factor in myelodysplastic syndromes", Nature Genetics, Jan. 1, 2012, vol. 44, pp. 53-59.
Gu, Z., et al., "Protein arginine methyltransferase 5 is essential for growth of lung cancer cells", Biochem J., (2012), pp. 235-241, vol. 446, No. 2.
Guo et al., "Sting Agonists Induce an Innate Antiviral Immune Response against Hepatitis B Virus", Antimicrobial Agents and Chemotherapy vol. 59, No. 2, Feb. 1, 2015, 1273-1281.
Hsu, J.M., et al., "Crosstalk between Arg 1175 methylation and Tyr 1173 phosphorylation negatively modulates EGFR-mediated ERK activation", Nature Cell Biology, (2011), pp. 174-181, vol. 13, No. 2.
Hu, H., et al., "Small Molecule Inhibitors of Protein Arginine Methyltransferase", Expert Opinion on Investigational Drugs, (2016), pp. 335-358, vol. 25, No. 3.
HUGO Gene Nomenclature Committee (HGNC) reports for the Major Spliceosome found online at https://www.genenames.org/data/genegroup/#!/group/1518 and accessed Apr. 20, 2021.
International Report on Patentability; International Patent Application No. PCT/EP2016/070097; dated Feb. 27, 2018.
International Search Report relating to International Patent Application No. PCT/EP2016/070097, filed on Aug. 25, 2016, dated Oct. 12, 2016.
International Search Report relating to International Patent Application No. PCT/EP2017/054324, filed on Feb. 24, 2017, dated May 2, 2017.
International Search Report relating to International Patent Application No. PCT/EP2017/074983, filed on Oct. 2, 2017, dated Nov. 16, 2017.
International Search Report relating to International Patent Application No. PCT/EP2018/054644, filed on Feb. 26, 2018, dated May 3, 2018.
Jansson, M., et al., "Arginine methylation regulates the p53 response", Nature Cell Biology, (2008), pp. 1431-1439, vol. 10, No. 12.
Karkhanis, V., et al., "Versatility of PRMT5-induced methylation in growth control and development", Trends in Biochemical Sciences, (2011), pp. 633-641, vol. 36, No. 12.
Kung, P.P., et al., "Design, synthesis, and biological evaluation of novel human 5'-deoxy-5'-methylthioadenosine phosphorylase (MTAP) substrates", Bioorganic & Medicinal Chemistry Letters, (2005), pp. 2829-2833, vol. 15.
Li, et al., A patent review of arginine methyltransferase inhibitors, Expert Opinion on Therapeutic Patents, 2019, vol. 29, No. 2, pp. 97-114.
March, J., "Advanced Organic Chemistry—Reactions, Mechanisms, and Structure", John Wiley & Sons, Inc., (2002), 4th Edition, A Wiley-Interscience Publication, see Table of Contents.
Matsubara, S., et al., "[2+1] Cycloaddition reaction of bis(iodozincio)methane with 1,2-diketones: face-to-face complex of bis(iodozincio)methane and 1,2-diketones as a reaction intermediate", Tetrahedron, (2002), pp. 8255-8262, vol. 58.
Moukha-Chafiq, O., et al., "Synthesis and General Biological Activity of a Small Adenosine-5'-(Carboxamide and Sulfanilamide) Library", Nucleosides, Nucleotides and Nucleic Acids, (2014), pp. 709-729, vol. 33, No. 11.
Pal, S., et al., "Low levels of miR-92b/96 induce PRMT5 translation and H3R3 methylation in mantle cell lymphoma", The EMBO Journal, (2007), pp. 3558-3569, vol. 26, No. 15.
Penebre, E., et al., "Identification of a First-in-Class PRMT5 Inhibitor with Potent in Vitro and in Vivo Activity in Preclinical Models of Mantle Cell Lymphoma", Blood, (2014), see Abstract.
Prasad, R.N., et al., "Modification of the 5' Position of Purine Nucleosides. 2. Synthesis and Some Cardiovascular Properties of Adenosine-5'-(N-substituted)carboxamides1,2", J. Med. Chem., (1980), pp. 313-319, vol. 23, No. 3.
Schmidt, R.R., et al., "Synthese 5'-modifizierter Adenosinderivate", Chemische Berichte, (1968), pp. 590-594, vol. 101, No. 2.
Shendure, J., et al., "Next-generation DNA sequencing", Nature Biotechnolgoy, (2008), pp. 1135-1145, vol. 26, No. 10.

(56) References Cited

OTHER PUBLICATIONS

Shilo, K., et al., "Cellular localization of protein arginine methyltransferase-5 correlates with grade of lung tumors", Diagnostic Pathology, (2013), pp. 1-9, vol. 8, No. 201.
Stahl, p. H., et al., "Handbook of Pharmaceutical Salts: Properties, Selection, and Use", Journal of Medicinal Chemistry, Book Reviews, (2003), pp. 1277-1278, vol. 46, No. 7.
Stopa, N., et al., "The PRMT5 arginine methyltransferase: many roles in development, cancer and beyond", Cell. Mol. Life Sci., (2015), pp. 2041-2059, vol. 72, No. 11.
Tiwari et al. Synthesis and Anticancer Evaluation of 4'-C-Methyl-2'-Fluoro Arabino Nucleosides, Nucleotides and Nucleic Acids (2009), vol. 28, Nos. 5-7, pp. 657-677.
Vuilhorgne, M., et al., "New Synthetic S-Adenosyl-Homocysteine Analogues with Oncostatic and Antiviral Activity". Heterocylces, 1978, pp. 495-520, vol. 11, XP009112700.
Wang, L., et al., "Protein Arginine Methyltransrerase 5 Suppresses the Transcription of the RB Family of Tumor Suppressors in Leukemia and Lymphoma Cells", Molecular and Cellular Biology, (2008), pp. 6262-6277, vol. 28, No. 20.
Wang, Q., et al., "Identification of a Novel Protein Arginine Methyltransferase 5 Inhibitor in Non-small Cell Lung Cancer by Structure-Based Virtual Screening", Frontiers in Pharmacology, (2018), pp. 1-10, vol. 9, article 173.
Wei, H., et al., "PRMT5 dimethylates R30 of the p65 subunit to activate NF-KB", Proc Natl Acad Sci USA, (2013), pp. 13516-13521, vol. 110, No. 33.
Wei, T.Y.W., et al., "Methylosome protein 50 promotes androgen- and estrogen-independent tumorigenesis", Cellular Signaling, (2014), pp. 2940-2950, vol. 26.
Brand et al., "Synthesis of [n,5]-Spiroketals by Ring Enlargement of Donor-Acceptor-Substituted Cyclopropane Derivatives," JOC, 2009, vol. 74, Issue 22, pp. 8779-8786.
Brehmer et al., "Abstract DDT02-04: A novel PRMT5 inhibitor with potent in vitro and in vivo activity in preclinical lung cancer models", Experimental and Molecular Therapeutics, 2017, AACR Annual Meeting, pp. 1-4.
CAS 1152172-19-4, Dated Jan. 18, 2022.
CAS 1259070-80-8, Dated Jan. 7, 2022.
CAS 33985-40-9, Dated Jan. 12, 2022.
CAS 3680-69-1, Dated Jan. 11, 2022.
CAS 514206-18-9, Dated Jan. 18, 2022.
CAS 54622-95-6, Dated Jan. 14, 2022.
CAS 56613-80-0, Dated Jan. 14, 2022.
CAS 58-61-7, Dated Jan. 11, 2022.
CAS 6991-65-7, Data Feb. 2, 2022.
CAS 78922-04-0, Dated Jan. 11, 2022.
CAS 808744-34-5, Dated Jan. 15, 2022.
CAS 87-42-3, Dated Jan. 11, 2022.
CAS 95408-45-0, Dated Jan. 15, 2022.
Cheson et al., "Clinical Application And Proposal For Modification Of The International Working Group (IWG) Response Criteria In Myelodysplasia", Blood, 2006, vol. 108 No. 2, pp. 419-425.
Eisenhauer et al., "New Response Evaluation Criteria In Solid Tumours: Revised RECIST Guideline (Version 1.1).", European Journal of Cancer, 2009, vol. 45, pp. 228-247.
Fitchen, J.H, et al. "Methylthioadenosine phosphorylase deficiency in human leukemias and solid tumors," Cancer research. vol. 46, No. 10, Oct. 1986, pp. 5409-5412.
Gerhart et al., "Activation of the p53-MDM4 Regulatory Axis Defines The Anti-Tumour Response To PRMT5 Inhibition Through Its Role In Regulating Cellular Splicing", Scientific Reports, Jun. 2018, vol. 8 No. 1, pp. 1-15, XP055625791.
Guo et al., "Abstract 3905: Translational Efficacy And Safety Modeling And Simulation To Support The Clinical Development Of JNJ-64619178, a PRMT5 Inhibitor", Cancer Research, AACR Annual Meeting 2019, vol. 79, Suppl. 13, pp. 1-4.

International Search Report and Written Opinion relating to International Patent Application No. PCT/EP2020/065639, filed Jun. 5, 2020, dated Aug. 26, 2020.
Lin et al., "Nucleoside Protein Arginine Methyl Transferase 5 (PRMT5) Inhibitors.", Bioorganic & Medicinal Chemistry Letters, 2019, vol. 29 No. 11, pp. 1264-1269, XP055663652.
Millar et al., "Abstract 950: In Vivo Efficacy And Pharmacodynamic Modulation Of JNJ-64619178, A Selective PRMT5 Inhibitor, In Human Lung And Hematologic Preclinical Models", Cancer Research Annual Meeting 2019, AACR; Cancer Res 2019, vol. 79, Suppl. 13, Abstract No. 950, pp. 1-4.
Nobori T, et al. "Methylthioadenosine phosphorylase deficiency in human non-small cell lung cancers". Cancer research. vol. 53, No. 5, Mar. 1, 1993, pp. 1098-1101.
Nobori, T, et al. "Genomic cloning of methylthioadenosine phosphorylase: a purine metabolic enzyme deficient in multiple different cancers". Proceedings of the National Academy of Sciences, vol. 93, No. 12, Jun. 11, 1996, pp. 6203-6208.
Nowak et al., "Addition of Difluorocarbene to 4',5'-Unsaturated Nucleosides: Synthesis and Deoxygenation Reactions of Difluorospirocyclopropane Nucleosides," JOC, 2006, vol. 71, pp. 8876-8883.
Ramakrishma et al., "Stereoselective Synthesis Of 1,6-Dioxaspirolactones From Spiro-Cyclopropanecarboxylated Sugars: Total Synthesis Of Dihydro-Pyrenolide D," RSC Adv., 2015, vol. 5, pp. 8142-8145.
Reagan-Shaw et al., "Dose translation from animal to human studies revisited", The FASEB Journal, 2007, vol. 22, pp. 659-661.
Redlich et al., "Chiral Cyclobutanones by [2+2]-Cycloaddition of Dichloroketene to Carbohydrate Enol Ethers," Angewe Chem., Int. Ed. Engl., 1989, vol. 28, pp. 777-778.
Wilting et al., "Epigenetic Mechanisms In Tumorigenesis, Tumor Cell Heterogeneity And Drug Resistance", Drug Resistance Updates, 2012, vol. 15, pp. 21-38.
Written Opinion of the International Search Authority relating to International Patent Application No. PCT/EP2016/070097, filed on Aug. 25, 2016, dated Oct. 12, 2016.
Written Opinion of the International Search Authority relating to International Patent Application No. PCT/EP2018/054644, filed on Feb. 26, 2018, dated May 3, 2018.
Wu et al., "Abstract 4859: JNJ-64619178, a Selective And Pseudo-Irreversible PRMT5 Inhibitor With Potent Invitro And Invivo Activity, Demonstrated In Several Lung Cancer Models.", Experimental and Molecular Therapeutics, Jul. 2018, pp. 1-4, XP055668420, Retrieved from the Internet: URL:https://www.semanticscholar.org/paper/Abstract-4859:-JNJ-64619178,-a-selective-and-PRMT5-Wu-Millar/a6583b4db0edbaefacf2 888b121f87e020d6889e.
Wuts et al., "Protective Groups in Organic Synthesis," Fourth Edition, Wiley, New York, 2006, pp. 1-1112.
Written Opinion of the International Search Authority relating to International Patent Application No. PCT/EP2017/054324, filed on Feb. 24, 2017, dated May 2, 2017.
Written Opinion PCT/EP2017/074983, dated Nov. 16, 2017.
Written Opinion relating to International Patent Application PCT/EP2016/070097, filed Aug. 25, 2016, dated Oct. 12, 2016.
Xiong, et al., Driver Genes as Targets for Lung Cancer Prevention and Treatment Progress in Chemistry, Sep. 9, 2013, vol. 25, pp. 1517-1525.
Zhao, Q., et al., "PRMT5-mediated methylation of histone H4R3 recruits DNMT3A, coupling histone and DNA methylation in gene silencing", Nat Struct Mol Biol, (2009), pp. 304-311, vol. 16, No. 3.
Secrist et al., "Syntheses of 5'-Substituted Analogs of Carbocyclic 3-Deazaadenosine as Potential Antivirals", J. Med. Chem., Jan. 19, 1993, vol. 36, pp. 2102-2106.
U.S. Appl. No. 16/487,852, filed Aug. 22, 2019.

\* cited by examiner

USE OF BIOMARKERS IN IDENTIFYING CANCER PATIENTS THAT WILL BE RESPONSIVE TO TREATMENT WITH A PRMT5 INHIBITOR

CROSS-REFERENCE TO RELATED APPLICATIONS

This application is a divisional of U.S. patent application Ser. No. 16/487,852 filed on Aug. 22, 2019, now U.S. Pat. No. 11,279,970, which is a U.S. national stage of PCT Application No. PCT/EP2018/054644, filed Feb. 26, 2018, which claims the benefit of priority of U.S. patent application Ser. No. 62/464,006, filed Feb. 27, 2017, which are incorporated by reference herein, in their entireties and for all purposes.

TECHNICAL FIELD

Provided herein are methods of identifying a patient with a high likelihood to be responsive to treatment with a protein arginine N-methyltransferase 5 inhibitor and methods of treating the same.

BACKGROUND

Protein arginine N-methyltransferase 5 (PRMT5), also described as Hs17, Jbp1, Skb1, Capsuleen or Dart5, is one of the major methyltransferases responsible for mono- and symmetric dimethylation of arginines. PRMT5 belongs to the Sym Arg Dimethyltransferase enzyme family. Catalytic activity is linked to oncogenic lung driver pathway activation (splicing & WNT signalling) and epigenetic repression of tumour suppressors as well as tumour immunogenic chemokines. Protein level and localisation correlate with higher cellular methylation, loss of the bronchial epithelial phenotype and poor disease progression.

Post-translational arginine methylation on histones and non-histone proteins is crucial for a variety of biological processes, like genome organization, transcription, differentiation, spliceosome function, signal transduction and regulation of cell-cycle progression, stem cells and T-cell fate. Metazoan PRMT5 forms a functional complex with the methylosome protein 50 (MEP50) also named as Wdr77, androgen receptor coactivator p44 and Valois. Both, elevated PRMT5-MEP50 protein level and cytoplasmic accumulation are implicated in cancer tumorigenesis and have recently been correlated with poor clinical outcome. Cellular rescue experiments that addressed both the catalytic and scaffold function of the PRMT5-MEP50 complex, beside comprehensive enzymological studies have substantiate the oncogenic link between protein level, localization and enzymatic function. This correlation turns PRMT5 into an essential small molecule drug target against cancer and other diseases.

PRMT5 is a member of the type II PRMT subfamily that utilizes S-adenosylmethionine (SAM) to generate symmetric dimethylated arginine on histones and non-histone protein substrates and S-adenosylhomocysteine (SAH). The regulation of PRMT5 activity occurs through a vast number of different binding partners, post-translational modifications, miRNAs and subcellular localization. Methylation of histones H2A and H4 on Arg3 and histone H3 on Arg8 regulate chromatin organization for specific repression/activation of gene transcripts that are involved in differentiation, transformation, cell-cycle progression and tumor suppression. Furthermore, PRMT5-mediated methylation of histone H4 on Arg3 might recruit the DNA-methyltransferase DNMT3A to couple histone and DNA methylation for long-term gene silencing.

Non-histone methylation can occur either in the cytoplasm or nucleus dependent on the cellular localization of PRMT5. The methylation of the Sm proteins D1 and D3, which are required for the assembly of the nuclear spliceosome, takes place in the cytoplasm as part of the PRMT5 containing "methylosome". Further evidence that PRMT5 is involved in splicing, was provided by the conditional PRMT5 knockout in mouse neural stem cells. Cells that lack PRMT5 showed a selective retention of introns and skipping of exons with weak 5' donor sites. In addition to a role in splicing, PRMT5 influences key pathways involved in cell fate and homeostasis by direct methylation of key signaling nodules like p53,30 EGFR,26 CRAF,3 PI3K/AKT,64 and NFkB.

Since PRMT5 is one of the major sym-Arg methyltransferases and involved in a multitude of cellular processes, an increased protein expression appears to be an important factor in its tumorigenicity. Interestingly, the translation of PRMT5 in mantle cell lymphoma (MCL) seems to be regulated by miRNAs. Although MCL cells show less mRNA and a slower transcription rate of PRMT5 than normal B lymphocytes, the PRMT5 level and the methylation of H3R8 and H4R3 are significantly increased. Re-expression of miRNAs that binds the 3'UTR region of PRMT5 decreases PRMT5 protein level. Strikingly, a PRMT5 antisense RNA has been found within the human PRMT5 gene that supports the hypothesis of a specific translational regulation rather than high mRNA expression level.

Although PRMT5 is highly considered as a clinical relevant target, very few selective PRMT5 inhibitors have been published yet. Recently, a novel sub-nanomolar potent PRMT5 inhibitor (EPZ015666) with anti-tumor activity in multiple MCL xenograft models has been described to be the first chemical probe suitable for further validation of PRMT5's biology and role in cancer (Chan-Penebre E, Kuplast K G, Majer C R, et al. A selective inhibitor of PRMT5 with in vivo and in vitro potency in MCL models. Nat Chem Biol. June 2015; 11(6):432-437).

WO2014100695A1 discloses compounds useful for inhibiting PRMT5 activity; Methods of using the compounds for treating PRMT5-mediated disorders are also described.

WO2014100730A1 discloses PRMT5 inhibitors containing a dihydro- or tetrahydroisoquinoline and uses thereof.

Devkota, K. et al., ACS Med Chem Lett, 2014. 5: p. 293-297, describes the synthesis of a series of analogues of the natural product sinefungin and the ability of these analogues to inhibit EHMT1 and EHMT2.

WO2003070739 discloses partial and full agonists of Al adenosine receptors, their preparation, and their therapeutic use.

WO2012082436 discloses compounds and compositions as modulators of histone methyltransferases, and for treating diseases influenced by modulation of histone methyltransferase activity.

WO2014100719 discloses PRMT5 inhibitors and uses thereof.

WO03074083 discloses combination therapies that selectively kill methylthioadenosine phosphorylase deficient cells, Analogs of MTA are described herein as anti-toxicity agents.

Kung, P.-P. et al., Bioorg Med Chem Lett, 2005. 15: p. 2829-2833, describes the design, synthesis, and biological evaluation of novel human 5'-deoxy-5'-methylthioadenosine phosphorylase (MTAP) substrates.

WO2012075500 discloses 7-deazapurine modulators of histone methyltransferase.

WO2014035140 discloses compounds and compositions for modulating histone methyltransferase activity.

WO2015200680 describes PRMT5 inhibitors and uses thereof.

WO2017/032840 and WO2017/153186 also describe PRMT5 inhibitors and uses thereof and are incorporated by reference herein.

PRMT5 has been linked to lung cancer through multiple mechanisms. Elevated PRMT5 and MEP50 expression in NSCLC is highly correlated with poorer survival. Mechanistic insight into this elevated expression in lung adenocarcinoma was shown by studies in which high cytoplasmic expression of PRMT5 was directly correlated with poor prognosis, possibly mediated through the epithelial-to mesenchymal transition and histone methylation. In addition, PRMT5 overexpression causes the formation of tumors in nude mice. The mechanism behind the cell-transforming capabilities of PRMT5 is unclear, but the enzyme is postulated to have roles in cell death, cell cycle progression, splicing, cell growth and proliferation.

Preclinical data demonstrates that PRMT5 inhibition causes lung cancer cell death of a subset of lung cancer population while different subsets are unaffected by long exposure to PRMT5 inhibitor. Therefore, there is a clear need for pharmacodynamic (PD) and/or predictive biomarkers to determine whether a particular patient's PRMT5 mediated disease has a high likelihood to respond to treatment with a PRMT5 inhibitor, or to measure pharmacodynamics effects of a treatment with a PRMT5 inhibitor in a patient with NSCLC or SCLC or other diseases mediated by PRMT5. No such biomarkers are currently known.

SUMMARY

Disclosed herein are methods of identifying a patient that will have a high likelihood to be responsive to treatment with a protein arginine N-methyltransferase 5 (PRMT5) inhibitor.

PRMT5 inhibitors may bind to the PRMT5 enzyme, competitively with natural substrate SAM (S-adenosyl-L-methionine), to inhibit such enzyme.

It is therefore anticipated that PRMT5 inhibitors or pharmaceutical compositions thereof may be useful for treating or preventing, in particular treating, diseases such as a blood disorder, metabolic disorders, autoimmune disorders, cancer, inflammatory diseases, cardiovascular diseases, neurodegenerative diseases, pancreatitis, multiorgan failure, kidney diseases, platelet aggregation, sperm motility, transplantation rejection, graft rejection, lung injuries and the like.

In particular, PRMT5 inhibitors or pharmaceutical compositions thereof may be useful for treating or preventing, in particular treating, of diseases such as allergy, asthma, hematopoietic cancer, lung cancer, prostate cancer, melanoma, metabolic disorder, diabetes, obesity, blood disorder, sickle cell anemia, and the like.

PRMT5 inhibitors or pharmaceutical compositions thereof may be useful for treating or preventing, in particular treating, of diseases such as a proliferative disorder, such as an autoimmune disease, cancer, a benign neoplasm, or an inflammatory disease.

PRMT5 inhibitors or pharmaceutical compositions thereof may be useful for treating or preventing, in particular treating, of diseases such as a metabolic disorder comprising diabetes, obesity; a proliferative disorder comprising cancer, hematopoietic cancer, lung cancer, prostate cancer, melanoma, or pancreatic cancer; blood disorder; hemoglobinopathy; sickle cell anemia; β-thalessemia, an inflammatory disease, and autoimmune disease e.g. rheumatoid arthritis, systemic lupus erythematosus, Sjogren's syndrome, diarrhea, gastroesophageal reflux disease, and the like.

In some embodiments, the inhibition of PRMT5 may be useful in treating or preventing, in particular treating, the following non-limiting list of cancers: breast cancer, lung cancer, esophageal cancer, bladder cancer, hematopoietic cancer, lymphoma, medulloblastoma, rectum adenocarcinoma, colon adenocarcinoma, gastric cancer, pancreatic cancer, liver cancer, adenoid cystic carcinoma, lung adenocarcinoma, head and neck squamous cell carcinoma, brain tumors, hepatocellular carcinoma, renal cell carcinoma, melanoma, oligodendroglioma, ovarian clear cell carcinoma, and ovarian serous cystadenoma.

Examples of metabolic disorders which may be treated or prevented, in particular treated, include, but are not limited to, diabetes or obesity.

Examples of blood disorders which may be treated or prevented, in particular treated, include, but are not limited to, hemoglobinopathy, such as sickle cell disease or β-thalassemia.

Examples of cancers which may be treated or prevented, in particular treated, include, but are not limited to, acoustic neuroma, adenocarcinoma, adrenal gland cancer, anal cancer, angiosarcoma (e.g., lymphangio sarcoma, lymphangioendothelio sarcoma, hemangio sarcoma), appendix cancer, benign monoclonal gammopathy, binary cancer (e.g., cholangiocarcinoma), bladder cancer, breast cancer (e.g., adenocarcinoma of the breast, papillary carcinoma of the breast, mammary cancer, medullary carcinoma of the breast), brain cancer (e.g., meningioma; glioma, e.g., astrocytoma, oligodendroglioma; medulloblastoma), bronchus cancer, carcinoid tumor, cervical cancer (e.g., cervical adenocarcinoma), chordoma, choriocarcinoma, craniopharyngioma, colorectal cancer (e.g., colon cancer, rectal cancer, colorectal adenocarcinoma), epithelial carcinoma, ependymoma, endothelio sarcoma (e.g., Kaposi's sarcoma, multiple idiopathic hemorrhagic sarcoma), endometrial cancer (e.g., uterine cancer, uterine sarcoma), esophageal cancer (e.g., adenocarcinoma of the esophagus, Barrett's adenocarinoma), Ewing sarcoma, eye cancer (e.g., intraocular melanoma, retinoblastoma), familiar hypereosinophilia, gall bladder cancer, gastric cancer (e.g., stomach adenocarcinoma), gastrointestinal stromal tumor (GIST), head and neck cancer (e.g., head and neck squamous cell carcinoma, oral cancer (e.g., oral squamous cell carcinoma (OSCC), throat cancer (e.g., pharyngeal cancer, laryngeal cancer, nasopharyngeal cancer, oropharyngeal cancer)), hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma (DLBCL)), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., "Waldenstrom's macro globulinemia"), immunoblastic large cell lymphoma, hairy cell leukemia (HCL), precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungiodes, Sezary syndrome), angioimmunoblastic T-cell lymphoma, extranodal natural killer T-cell lymphoma, enteropathy type T-cell lymphoma, subcutaneous panniculitis-like T-cell lymphoma, anaplastic large cell lymphoma); a mixture of one or more leukemia/lymphoma as described above; and multiple myeloma (MM)), heavy chain disease (e.g., alpha chain disease, gamma chain disease, mu chain disease), hemangioblastoma, inflammatory myofibroblastic tumors, immunocytic amyloidosis, kidney cancer (e.g., nephroblastoma a.k.a. Wilms' tumor, renal cell carcinoma), liver cancer (e.g., hepatocellular cancer (HCC), malignant hepatoma), lung cancer (e.g., bronchogenic carcinoma, non-small cell lung cancer (NSCLC), squamous lung cancer (SLC), adenocarcinoma of the lung, Lewis lung carcinoma, lung neuroendocrine tumors: typical carcinoid, atypical carcinoid, small cell lung cancer (SCLC), and large cell neuroendocrine carcinoma), leiomyosarcoma (LMS), mastocytosis (e.g., systemic mastocytosis), myelodysplastic syndromes (MDS), mesothelioma, myeloproliferative disorder (MPD) (e.g., polycythemia Vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)), neuroblastoma, neurofibroma (e.g., neurofibromatosis (NF) type 1 or type 2, schwannomatosis), neuroendocrine cancer (e.g., gastroenteropancreatic neuroendoctrine tumor (GEP-NET), carcinoid tumor), osteosarcoma, ovarian cancer (e.g., cystadenocarcinoma, ovarian embryonal carcinoma, ovarian adenocarcinoma), papillary adenocarcinoma, pancreatic cancer (e.g., pancreatic andenocarcinoma, intraductal papillary mucinous neoplasm (IPMN), Islet cell tumors), penile cancer (e.g., Paget's disease of the penis and scrotum), pinealoma, primitive neuroectodermal tumor (PNT), prostate cancer (e.g., prostate adenocarcinoma), rectal cancer, rhabdomyosarcoma, salivary gland cancer, skin cancer (e.g., squamous cell carcinoma (SCC), keratoacanthoma (KA), melanoma, basal cell carcinoma (BCC)), small bowel cancer (e.g., appendix cancer), soft tissue sarcoma (e.g., malignant fibrous histiocytoma (MFH), liposarcoma, malignant peripheral nerve sheath tumor (MPNST), chondrosarcoma, fibrosarcoma, myxosarcoma), sebaceous gland carcinoma, sweat gland carcinoma, synovioma, testicular cancer (e.g., seminoma, testicular embryonal carcinoma), thyroid cancer (e.g., papillary carcinoma of the thyroid, papillary thyroid carcinoma (PTC), medullary thyroid cancer), urethral cancer, vaginal cancer, and vulvar cancer (e.g., Paget's disease of the vulva).

Examples of neurodegenerative diseases which may be treated or prevented, in particular treated, include, but are not limited to, motor neurone disease, progressive supranuclear palsy, corticobasal degeneration, Pick's disease, Alzheimer's disease, AIDS-related dementia, Parkinson's disease, amyotropic lateral sclerosis, retinitis pigmentosa, spinal muscular atropy, and cerebellar degeneration.

Examples of cardiovascular diseases which may be treated or prevented, in particular treated, include, but are not limited to, cardiac hypertrophy, restenosis, atherosclerosis, and glomerulonephritis.

Examples of inflammatory diseases which may be treated or prevented, in particular treated, include, but are not limited to, inflammation associated with acne, anemia (e.g., aplastic anemia, haemolytic autoimmune anaemia), rhinitis, asthma, arteritis (e.g., polyarteritis, temporal arteritis, periarteritis nodosa, Takayasu's arteritis), arthritis (e.g., crystalline arthritis, osteoarthritis, psoriatic arthritis, gouty arthritis, reactive arthritis, rheumatoid arthritis and Reiter's arthritis), upper respiratory tract disease, ankylosing spondylitis, amylosis, amyotrophic lateral sclerosis, autoimmune diseases, allergies or allergic reactions, atherosclerosis, bronchitis, bursitis, chronic prostatitis, conjunctivitis, Chagas disease, chronic obstructive pulmonary disease, diverticulitis, cermatomyositis, diabetes (e.g., type I diabetes mellitus, type 2 diabetes mellitus), a skin condition (e.g., psoriasis, eczema, eczema hypersensitivity reactions, burns, dermatitis, pruritus (itch)), endometriosis, Guillain-Barre syndrome, infection, ischaemic heart disease, Kawasaki disease, glomerulonephritis, gingivitis, hypersensitivity, headaches (e.g., migraine headaches, tension headaches), ileus (e.g., postoperative ileus and ileus during sepsis), idiopathic thrombocytopenic purpura, interstitial cystitis (painful bladder syndrome), gastrointestinal disorder (e.g., selected from peptic ulcers, regional enteritis, diverticulitis, gastrointestinal bleeding, eosinophilic gastrointestinal disorders (e.g., eosinophilic esophagitis, eosinophilic gastritis, eosinophilic gastroenteritis, eosinophilic colitis), gastritis, diarrhea, gastroesophageal reflux disease (GORD, or its synonym GERD), inflammatory bowel disease (IBD) Crohn's disease, ulcerative colitis, collagenous colitis, lymphocytic colitis, ischaemic colitis, diversion colitis, Behcet's syndrome, indeterminate colitis) and inflammatory bowel syndrome (IBS)), lupus, morphea, myeasthenia gravis, myocardial ischemia, multiple sclerosis, nephrotic syndrome, pemphigus vulgaris, pernicious aneaemia, peptic ulcers, polymyositis, primary biliary cirrhosis, neuroinflammation associated with brain disorders (e.g., Parkinson's disease, Huntington's disease, and Alzheimer's disease), prostatitis, chronic inflammation associated with cranial radiation injury, pelvic inflammatory disease, reperfusion injury, regional enteritis, rheumatic fever, systemic lupus erythematosus, schleroderma, scierodoma, sarcoidosis, spondyloarthopathies, Sjogren's syndrome, thyroiditis, transplantation rejection, tendonitis, trauma or injury (e.g., frostbite, chemical irritants, toxins, scarring, burns, physical injury), vasculitis, vitiligo and Wegener's granulomatosis.

In particular, the inflammatory disease can be an acute inflammatory disease (e.g., for example, inflammation resulting from infection). In particular, the inflammatory disease can be a chronic inflammatory disease (e.g., conditions resulting from asthma, arthritis and inflammatory bowel disease). PRMT5 inhibitors may also be useful in treating inflammation associated with trauma and non-inflammatory myalgia. The compounds may also be useful in treating inflammation associated with cancer.

Examples of autoimmune diseases which may be treated or prevented, in particular treated, include, but are not limited to, arthritis (including rheumatoid arthritis, spondyloarthopathies, gouty arthritis, degenerative joint diseases such as osteoarthritis, systemic lupus erythematosus, Sjogren's syndrome, ankylosing spondylitis, undifferentiated spondylitis, Behcet's disease, haemolytic autoimmune anaemias, amyotrophic lateral sclerosis, amylosis, multiple sclerosis, acute painful shoulder, psoriatic, and juvenile arthritis), asthma, atherosclerosis, osteoporosis, bronchitis, tendonitis, bursitis, skin condition (e.g., psoriasis, eczema, eczema hypersensitivity reactions, burns, dermatitis, pruritus (itch)), enuresis, eosinophilic disease, gastrointestinal disorder (e.g., selected from peptic ulcers, regional enteritis, diverticulitis, gastrointestinal bleeding, eosinophilic gastrointestinal disorders (e.g., eosinophilic esophagitis, eosinophilic gastritis, eosinophilic gastroenteritis, eosinophilic colitis), gastritis, diarrhea, gastroesophageal reflux disease (GORD, or its synonym GERD), inflammatory bowel disease (IBD) (e.g., Crohn's disease, ulcerative colitis, collagenous colitis, lymphocytic colitis, ischaemic colitis, diversion colitis, Behcet's syndrome, indeterminate colitis) and inflammatory bowel syndrome (IBS)), and disorders ameliorated by a gastroprokinetic agent (e.g., ileus, postoperative ileus and ileus during sepsis; gastroesophageal reflux disease (GORD, or its synonym GERD); eosinophilic esophagitis, gastroparesis such as diabetic gastroparesis; food intolerances and food allergies and other functional bowel disorders, such as non-ulcerative dyspepsia (NUD) and non-cardiac chest pain (NCCP, including costo-chondritis)).

In a particular embodiment, a PRMT5 inhibitor may be useful in somatic cell reprogramming, such as reprogramming somatic cells into stem cells. In a particular embodiment, a PRMT5 inhibitors may be useful in germ cell development, and are thus envisioned useful in the areas of reproductive technology and regenerative medicine.

Other diseases which may be treated or prevented, in particular treated, include, but are not limited to, ischemic injury associated myocardial infarctions, immunological diseases, stroke, arrhythmia, toxin-induced or alcohol related liver diseases, aspirin-sensitive rhinosinusitis, cystic fibrosis, cancer pain, and haematological diseases, for example chronic anemia and aplastic anemia.

The present invention thus comprises a method of identifying a patient that is likely to be responsive to treatment with a protein arginine N-methyltransferase 5 (PRMT5) inhibitor comprising evaluating a biological sample from the patient for the presence of any of the following:
a PIC3CA activating mutation,
a spliceosome alteration,
a cyclin D1 pathway amplicifation, and/or
a WNT pathway alteration
wherein the presence of any said mutation or alteration indicates a higher likelihood for said patient to be responsive to treatment with said PRMT5 inhibitor than in the absence of any said mutation or alteration.

In a preferred embodiment, the splicesosome alteration comprises a mutation in a gene selected from the group consisting of U2AF1, RBM10 and KIAA1429. In a specific embodiment, the gene is U2AF1 and the mutation is S34F. In another specific embodiment, the gene is RBM10 and the mutation is selected from the group consisting of I696fs, I348N, G840fs. In yet another specific embodiment, the gene is KIAA1429 and the mutation is selected from the group consisting of L837V, F1260L, D251if, T1333M, V1548L, G397A and Q962E. Other spliceosome alterations may also indicate a higher likelihood of the patient to be responsive to treatment with a PRMT5 inhibitor.

In another embodiment the PIC3CA activating mutation is selected from the group consisting of H1047R, PG106-R108del, T1025A and E542K. However, other activating mutation may also indicate a higher likelihood of the patient to be responsive to treatment with a PRMT5 inhibitor.

In another embodiment, the cyclin D1 pathway amplification is an amplification of Cyclin D1, CDK4 or CDK6 expression. However, other cyclin D1 pathway amplifications may also indicate a higher likelihood of the patient to be responsive to treatment with a PRMT5 inhibitor.

In another embodiment, the WNT pathway alteration comprises autocrine WNT signaling. Preferably, the WNT pathway alteration comprises a mutation in an APC or CTNNB1 gene. In a specific embodiment, the gene is APC and the mutation is selected from the group consisting of R213Q, R2673G, I1177M and D2796G. In another specific embodiment, the gene is CTNNB1 and the mutation is selected from the group consisting of Y670*, S45F, and T41A. However, other WNT pathway alterations may also indicate a higher likelihood of the patient to be responsive to treatment with a PRMT5 inhibitor.

In a particular embodiment, the mutation or alteration according to the invention comprises a spliceosome alteration, and the patient has NSCLC.

In another particular embodiment, the mutation or alteration according to the invention comprises a cyclin D1 pathway amplicifation or a WNT pathway alteration, and the patient has NSCLC.

In another particular embodiment, the mutation or alteration according to the invention comprises a PIC3CA activating mutation and the patient has SCLC.

In a preferred embodiment of the invention, the PRMT5 inhibitor is compound 2 or compound 80.

The present application discloses a sensitivity link to PI3K-alpha activating mutations in SCLC, and in spliceosome alterations and WNT pathway upregulation in NSCLC. Cyclin D1 pathway amplifications are associated with PRMT5 inhibitor response in NSCLC.

Kits and primers for identifying the presence of one or more mutation or alterations as described above in a biological sample are further provided herein.

The disclosed methods, kits, and primers may be understood more readily by reference to the following detailed description taken in connection with the accompanying figures, which form a part of this disclosure. It is to be understood that the disclosed methods, kits, and primers are not limited to the specific methods, kits, and primers described and/or shown herein, and that the terminology used herein is for the purpose of describing particular embodiments by way of example only and is not intended to be limiting of the claimed methods, kits, and primers.

Reference to a particular numerical value includes at least that particular value, unless the context clearly dictates otherwise. When a range of values is expressed, another embodiment includes from the one particular value and/or to the other particular value. Further, reference to values stated in ranges include each and every value within that range. All ranges are inclusive and combinable.

It is to be appreciated that certain features of the disclosed methods, kits, and primers which are, for clarity, described herein in the context of separate embodiments, may also be provided in combination in a single embodiment. Conversely, various features of the disclosed methods, kits, and primers that are, for brevity, described in the context of a single embodiment, may also be provided separately or in any subcombination.

As used herein, the singular forms "a," "an," and "the" include the plural.

As used herein, "treating" and like terms refer to reducing the severity and/or frequency of cancer symptoms, eliminating cancer symptoms and/or the underlying cause of said symptoms, reducing the frequency or likelihood of cancer symptoms and/or their underlying cause, and improving or remediating damage caused, directly or indirectly, by cancer.

"Biological samples" refers to any sample from a patient in which cancerous cells can be obtained and RNA can be isolated. Suitable biological samples include, but are not limited to, blood, lymph fluid, bone marrow, a solid tumor sample, or any combination thereof.

As used herein, "pre-amplification" refers to a PCR procedure that is performed prior to the amplifying step in order to increase the quantity of template cDNA for the amplification step. A pre-amplification step can be performed, for example, using the TaqMan® PreAmp Master Mix (Life Technologies/Applied Biosystems® product #4391128).

As used herein, "amplifying," "amplify," and like terms refer to the generation of numerous identical copies of a nucleic acid sample. Suitable techniques for amplifying a nucleic acid sample include, but are not limited to, polymerase chain reaction (PCR) and real-time polymerase chain reaction (RT-PCR). In some embodiments, the amplifying step comprises RT-PCR.

"Next-generation sequencing" or "NGS" refers to any sequencing method that determines the nucleotide sequence of either individual nucleic acid molecules (e.g., in single molecule sequencing) or clonally expanded proxies for individual nucleic acid molecules in a high throughput parallel fashion (e.g., greater than $10^3$, $10^4$, $10^5$ or more molecules can be sequenced simultaneously). Exemplary next generation sequencing techniques include sequencing by synthesis, sequencing by ligation, and sequencing by hybridization. Exemplary next generations sequencing methods include Massively Parallel Signature Sequencing (Lynx Therapeutics); 454 pyro-sequencing (454 Life Sciences/Roche Diagnostics); solid-phase, reversible dye-terminator sequencing (Solexa/Illumina); SOLiD technology (Applied Biosystems); Ion semiconductor sequencing (Ion Torrent); and DNA nanoball sequencing (Complete Genomics). Descriptions of certain NGS platforms can be found in the following: Shendure, et al, "Next-generation DNA sequencing," Nature, 2008, vol. 26, No. 10, 1135-1145;

NGS Platforms

In some embodiments, high throughput, massively parallel sequencing employs sequencing-by-synthesis with reversible dye terminators. In other embodiments, sequencing is performed via sequencing-by-ligation. In yet other embodiments, sequencing is single molecule sequencing. Examples of Next Generation Sequencing techniques include, but are not limited to pyrosequencing, Reversible dye-terminator sequencing, SOLiD sequencing, Ion semiconductor sequencing, Helioscope single molecule sequencing etc.

The Ion Torrent™ (Life Technologies, Carlsbad, Calif.) amplicon sequencing system employs a flow-based approach that detects pH changes caused by the release of hydrogen ions during incorporation of unmodified nucleotides in DNA replication. For use with this system, a sequencing library is initially produced by generating DNA fragments flanked by sequencing adapters. In some embodiments, these fragments can be clonally amplified on particles by emulsion PCR. The particles with the amplified template are then placed in a silicon semiconductor sequencing chip. During replication, the chip is flooded with one nucleotide after another, and if a nucleotide complements the DNA molecule in a particular microwell of the chip, then it will be incorporated. A proton is naturally released when a nucleotide is incorporated by the polymerase in the DNA molecule, resulting in a detectable local change of pH. The pH of the solution then changes in that well and is detected by the ion sensor. If homopolymer repeats are present in the template sequence, multiple nucleotides will be incorporated in a single cycle. This leads to a corresponding number of released hydrogens and a proportionally higher electronic signal.

The 454™ GS FLX™ sequencing system (Roche, Germany), employs a light-based detection methodology in a large-scale parallel pyrosequencing system. Pyrosequencing uses DNA polymerization, adding one nucleotide species at a time and detecting and quantifying the number of nucleotides added to a given location through the light emitted by the release of attached pyrophosphates. For use with the 454™ system, adapter-ligated DNA fragments are fixed to small DNA-capture beads in a water-in-oil emulsion and amplified by PCR (emulsion PCR). Each DNA-bound bead is placed into a well on a picotiter plate and sequencing reagents are delivered across the wells of the plate. The four DNA nucleotides are added sequentially in a fixed order across the picotiter plate device during a sequencing run. During the nucleotide flow, millions of copies of DNA bound to each of the beads are sequenced in parallel. When a nucleotide complementary to the template strand is added to a well, the nucleotide is incorporated onto the existing DNA strand, generating a light signal that is recorded by a CCD camera in the instrument.

Sequencing technology based on reversible dye-terminators: DNA molecules are first attached to primers on a slide and amplified so that local clonal colonies are formed. Four types of reversible terminator bases (RT-bases) are added, and non-incorporated nucleotides are washed away. Unlike pyrosequencing, the DNA can only be extended one nucleotide at a time. A camera takes images of the fluorescently labeled nucleotides, then the dye along with the terminal 3' blocker is chemically removed from the DNA, allowing the next cycle.

Helicos's single-molecule sequencing uses DNA fragments with added polyA tail adapters, which are attached to the flow cell surface. At each cycle, DNA polymerase and a single species of fluorescently labeled nucleotide are added, resulting in template-dependent extension of the surface-immobilized primer-template duplexes. The reads are performed by the Helioscope sequencer. After acquisition of images tiling the full array, chemical cleavage and release of the fluorescent label permits the subsequent cycle of extension and imaging.

Sequencing by synthesis (SBS), like the "old style" dye-termination electrophoretic sequencing, relies on incorporation of nucleotides by a DNA polymerase to determine the base sequence. A DNA library with affixed adapters is denatured into single strands and grafted to a flow cell, followed by bridge amplification to form a high-density array of spots onto a glass chip. Reversible terminator methods use reversible versions of dye-terminators, adding one nucleotide at a time, detecting fluorescence at each position by repeated removal of the blocking group to allow polymerization of another nucleotide. The signal of nucleotide incorporation can vary with fluorescently labeled nucleotides, phosphate-driven light reactions and hydrogen ion sensing having all been used. Examples of SBS platforms include Illumina GA and HiSeq 2000. The MiSeq® personal sequencing system (Illumina, Inc.) also employs sequencing by synthesis with reversible terminator chemistry.

In contrast to the sequencing by synthesis method, the sequencing by ligation method uses a DNA ligase to determine the target sequence. This sequencing method relies on enzymatic ligation of oligonucleotides that are adjacent through local complementarity on a template DNA strand. This technology employs a partition of all possible oligonucleotides of a fixed length, labeled according to the sequenced position. Oligonucleotides are annealed and ligated and the preferential ligation by DNA ligase for matching sequences results in a dinucleotide encoded color space signal at that position (through the release of a fluorescently labeled probe that corresponds to a known nucleotide at a known position along the oligo). This method is primarily used by Life Technologies' SOLiD™ sequencers. Before sequencing, the DNA is amplified by emulsion PCR. The resulting beads, each containing only copies of the same DNA molecule, are deposited on a solid planar substrate.

SMRT™ sequencing is based on the sequencing by synthesis approach. The DNA is synthesized in zero-mode wave-guides (ZMWs)-small well-like containers with the capturing tools located at the bottom of the well. The sequencing is performed with use of unmodified polymerase (attached to the ZMW bottom) and fluorescently labeled nucleotides flowing freely in the solution. The wells are constructed in a way that only the fluorescence occurring at the bottom of the well is detected. The fluorescent label is detached from the nucleotide at its incorporation into the DNA strand, leaving an unmodified DNA strand.

Primers for Amplifying Mutants

One skilled in the art knows that amplification of nucleic acid requires primers that are complementary, and bind to, a 5' and 3' region of the nucleic acid strand that flanks the region sought to be amplified. As used herein, "pair of primers" refers to the forward and reverse primers used in an amplifying step.

The person skilled in the art can identify suitable primers for amplification and detection of particular mutations as described above, using known methods.

Genomics and Analysis

Functional genomics and transcription analysis can be used for analyzing amplification of pathways and genes, using standard techniques and protocols.

PRMT5 Inhibitors for Use in the Disclosed Methods

Suitable PRMT5 inhibitors for use in the disclosed methods are provided herein. In some embodiments, if one or more mutations or amplifications including a PIC3CA activating mutation, a spliceosome alteration, a cyclin D1 pathway amplicifation, and/or a WNT pathway alteration are present in the sample, the patient can be treated with a PRMT5 inhibitor disclosed in PCT/EP2016/070097 (incorporated herein by reference), including any tautomeric or stereochemically isomeric form thereof, and a N-oxide thereof, a pharmaceutically acceptable salts thereof, or a solvate thereof (suitable R groups are also disclosed in PCT/EP2016/070097). In some aspects, for example, the patient can be treated with compound 2 or compound 80, including any tautomeric or stereochemically isomeric form thereof, and a N-oxide thereof, a pharmaceutically acceptable salts thereof or a solvate thereof. In some aspects, the pharmaceutically acceptable salt is a HCl salt.

In some embodiments, the patient can be treated with a PRMT5 inhibitor if one or more mutations or amplifications including a PIC3CA activating mutation, a spliceosome alteration, a cyclin D1 pathway amplicifation, and/or a WNT pathway alteration are present in the sample, wherein the PRMT5 inhibitor is an anti-PRMT5 antibody.

Salts can be synthesized from a parent compound that contains a basic or acidic moiety by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002, which is incorporated herein by reference. Generally, such salts can be prepared by reacting the free acid or base forms of these compounds with the appropriate base or acid in water or in an organic solvent, or in a mixture of the two; generally, nonaqueous media such as ether, ethyl acetate, ethanol, isopropanol, or acetonitrile are used. The PRMT5 inhibitors for use in the disclosed methods may exist as mono- or di-salts depending upon the pKa of the acid from which the salt is formed.

Acid addition salts may be formed with a wide variety of acids, both inorganic and organic. Examples of acid addition salts include salts formed with an acid including, but not limited to, acetic, 2,2-dichloroacetic, adipic, alginic, ascorbic (e.g. L-ascorbic), L-aspartic, benzenesulphonic, benzoic, 4-acetamidobenzoic, butanoic, (+) camphoric, camphor-sulphonic, (+)-(1S)-camphor-10-sulphonic, capric, caproic, caprylic, cinnamic, citric, cyclamic, dodecylsulphuric, ethane-1,2-disulphonic, ethanesulphonic, 2-hydroxyethanesulphonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrobromic, hydrochloric, hydriodic, isethionic, lactic (e.g. (+)-L-lactic, (±)-DL-lactic), lactobionic, maleic, malic, (−)-L-malic, malonic, (±)-DL-mandelic, methanesulphonic, naphthalenesulphonic (e.g. naphthalene-2-sulphonic), naphthalene-1,5 -disulphonic, 1-hydroxy-2-naphthoic, nicotinic, nitric, oleic, orotic, oxalic, palmitic, pamoic, phosphoric, propionic, L-pyroglutamic, pyruvic, salicylic, 4-amino-salicylic, sebacic, stearic, succinic, sulphuric, tannic, (+)-L-tartaric, thiocyanic, toluenesulphonic (e.g. p-toluenesulphonic), undecylenic and valeric acids, as well as acylated amino acids and cation exchange resins.

One particular group of salts consists of salts formed from acetic, hydrochloric, hydriodic, phosphoric, nitric, sulphuric, citric, lactic, succinic, maleic, malic, isethionic, fumaric, benzenesulphonic, toluenesulphonic, methanesulphonic (mesylate), ethanesulphonic, naphthalenesulphonic, valeric, acetic, propanoic, butanoic, malonic, glucuronic and lactobionic acids. Another group of acid addition salts includes salts formed from acetic, adipic, ascorbic, aspartic, citric, DL-Lactic, fumaric, gluconic, glucuronic, hippuric, hydrochloric, glutamic, DL-malic, methanesulphonic, sebacic, stearic, succinic and tartaric acids.

If the compound is anionic, or has a functional group which may be anionic (e.g., —COOH may be —COO⁻), then a salt may be formed with a suitable cation. Examples of suitable inorganic cations include, but are not limited to, alkali metal ions such as Na⁺ and K⁺, alkaline earth metal cations such as $Ca^{2+}$ and $Mg^{2+}$, and other cations such as $Al^{3+}$. Examples of suitable organic cations include, but are not limited to, ammonium ion (i.e., $NH_4^+$) and substituted ammonium ions (e.g., $NH_3R^+$, $NH_2R_2^+$, $NHR_3^+$, $NR_4^+$).

Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

Where the compounds contain an amine function, these may form quaternary ammonium salts, for example by reaction with an alkylating agent according to methods well known to the skilled person. Such quaternary ammonium compounds are within the scope of the disclosed compounds. Compounds containing an amine function may also form N-oxides. A reference herein to a compound that contains an amine function also includes the N-oxide. Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle. N-Oxides can be formed by treatment of the corresponding amine with an oxidizing agent such as hydrogen peroxide or a per-acid (e.g. a peroxycarboxylic acid), see for example *Advanced Organic Chemistry*, by Jerry March, 4$^{th}$ Edition, Wiley Interscience, pages. More particularly, N-oxides can be made by the procedure of L. W. Deady (*Syn. Comm.* (1977), 7, 509-514) in which the amine compound is reacted with m-chloroperoxybenzoic acid (MCPBA), for example, in an inert solvent such as dichloromethane.

As used herein, the term "solvate" means a physical association of the compound with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. The term "solvate" is intended to encompass both solution-phase and isolatable solvates. Non-limiting examples of suitable solvates include the disclosed compounds in combination with water, isopropanol, ethanol, methanol, DMSO, ethyl acetate, acetic acid or ethanolamine and the like. The compound may exert its biological effects while in solution.

Solvates are well known in pharmaceutical chemistry. They can be important to the processes for the preparation of a substance (e.g. in relation to their purification), the storage of the substance (e.g. its stability) and the ease of handling of the substance, and are often formed as part of the isolation or purification stages of a chemical synthesis. A person skilled in the art can determine by means of standard and long used techniques whether a hydrate or other solvate has formed by the isolation conditions or purification conditions used to prepare a given compound. Examples of such techniques include thermogravimetric analysis (TGA), differential scanning calorimetry (DSC), X-ray crystallography (e.g. single crystal X-ray crystallography or X-ray powder diffraction) and Solid State NMR (SS-NMR, also known as Magic Angle Spinning NMR or MAS-NMR). Such techniques are as much a part of the standard analytical toolkit of the skilled chemist as NMR, IR, HPLC and MS. Alternatively the skilled person can deliberately form a solvate using crystallisation conditions that include an amount of the solvent required for the particular solvate. Thereafter the standard methods described above, can be used to establish whether solvates had formed. Also encompassed are any complexes (e.g. inclusion complexes or clathrates with compounds such as cyclodextrins, or complexes with metals) of the PRMT5 inhibitor.

Furthermore, the compound may have one or more polymorph (crystalline) or amorphous forms.

The compounds include compounds with one or more isotopic substitutions, and a reference to a particular element includes within its scope all isotopes of the element. For example, a reference to hydrogen includes within its scope $^1H$, $^2H$ (D), and $^3H$ (T). Similarly, references to carbon and oxygen include within their scope respectively $^{12}C$, $^{13}C$ and $^{14}C$ and $^{16}O$ and $^{18}O$. The isotopes may be radioactive or non-radioactive. In one embodiment, the compounds contain no radioactive isotopes. Such compounds are preferred for therapeutic use. In another embodiment, however, the compound may contain one or more radioisotopes. Compounds containing such radioisotopes may be useful in a diagnostic context.

In some embodiments, the patient is treated with a PRMT5 inhibitor if one or more U2AF1 mutants are present in the sample, wherein the PRMT5 inhibitor is compound 2 or compound 80, or a pharmaceutically acceptable salt thereof or a solvate thereof.

Methods of Treating Cancer in a Patient

Disclosed herein are methods of treating cancer in a patient comprising: evaluating a biological sample from the patient for the presence of one or more mutations or amplifications including a PIC3CA activating mutation, a spliceosome alteration, a cyclin D1 pathway amplicifation, and/or a WNT pathway alteration; and treating the patient with a PRMT5 inhibitor if one or more mutations or amplifications including a PIC3CA activating mutation, a spliceosome alteration, a cyclin D1 pathway amplicifation, and/or a WNT pathway alteration are present in the sample.

The disclosed methods can be used to treat a variety of cancer types including, but not limited to, bladder cancer, metastatic bladder cancer, ovarian cancer, head and neck cancer, esophageal cancer, non-small-cell lung adenocarcinoma, non-small cell lung squamous cell carcinoma, prostate cancer, lung cancer, gastric cancer, urothelial carcinoma, small cell lung cancer, breast cancer, endometrial cancer, choleagiocarcinoma, glioblastoma, gliomas, colon carcinoma, sarcomas, solid tumors of squamous origin, and multiple myeloma.

In some embodiments, the evaluating step comprises: isolating RNA from a biological sample; synthesizing cDNA from the isolated RNA; pre-amplifying the cDNA; and amplifying the pre-amplified cDNA with a pair of primers that bind to and amplify one or more mutations including a PIC3CA activating mutation, a spliceosome alteration, a cyclin D1 pathway amplicifation, and/or a WNT pathway alteration.

Isolating RNA from the biological sample can be performed by a number of procedures known to one skilled in the art. In one embodiment, RNA can be isolated from the biological sample using an AllPrep DNA/RNA FFPE Kit from Qiagen (product #80234)

Synthesizing cDNA from isolated RNA can be performed by a number of procedures known to one skilled in the art. In one embodiment, cDNA can be synthesized from isolated RNA using a High Capacity cDNA Reverse Transcriptase Kit with RNase Inhibitor from ABI (product #4374966).

Pre-amplification of cDNA can be performed by a number of procedures known to one skilled in the art. Amplification procedures are well known in the art. In one embodiment, cDNA can be pre-amplified using a TaqMan® PreAmp Master Mix (Life Technologies/Applied Biosystems® product #4391128).

Suitable PRMT5 inhibitors for use in the treatment methods include those previously described herein.

Methods of Identifying a Cancer Patient that will be Responsive to Treatment with a are Protein Arginine N-methyltransferase 5 (PRMT5) Inhibitor Kits for Identifying the Presence of Mutant or Altered Genes Further disclosed are kits for identifying the presence of one or more mutations or amplifications including a PIC3CA activating mutation, a spliceosome alteration, a cyclin D1 pathway amplicifation, and/or a WNT pathway alteration in a biological sample comprising: pairs of primers having the sequences of combination thereof; and instructions for performing an assay to detect one or more mutations or amplifications including a PIC3CA activating mutation, a spliceosome alteration, a cyclin D1 pathway amplicifation, and/or a WNT pathway alteration.

The summary, as well as the following detailed description, is further understood when read in conjunction with the appended drawings. For the purpose of illustrating the disclosed methods, kits, and primers, there are shown in the drawings exemplary embodiments of the methods, kits, and primers; however, the methods, kits, and primers are not limited to the specific embodiments disclosed.

DETAILED DESCRIPTION OF ILLUSTRATIVE EMBODIMENTS

PRMT5 inhibitors compounds 2 and 80 as used in the examples are also exemplified in PCT/EP2016/070097.

Hereinafter, the term "rt", "r.t." or "RT" means room temperature; "Me" means methyl; "MeOH" means methanol; "Et" means ethyl; "EtOH" means ethanol; "NaH" means sodium hydride; "DEAD" means diethyl azodicarboxylate; "HMPT" means hexamethylphosphorous triamide; "Boc2O" means tert-butoxycarbonyl anhydride; "ButONO" means tert-butyl nitrite; "TosOH" means 4-methylbenzenesulfonic acid; "TosCl" means 4-methylbenzenesulfonyl chloride (also p-toluenesulfonyl chloride); "CMBP" means cyanomethylenetributylphosphorane; "DBAD" means di-tert-butyl azodicarboxylate; "LAH" means lithium aluminum hydride; "NaBH(AcO)3" or "NaBH(OAc)3" means sodium triacetoxyborohydride; "EtOAc" means ethyl acetate; "TEA" or "Et3N" means triethylamine; "DCM" means dichloromethane; "q.s." means quantum sufficit; "Int." Means intermediate; "MeCN" or "ACN" means acetonitrile; "DMF" means N,N-dimethyl formamide; "DMA" means N,N-dimethylacetamide; "DMF-DMA" means N,N-Dimethylformamide dimethyl acetal; "Pd(dppf)Cl2" means [1,1'-Bis(diphenylphosphino)ferrocene]dichloropalladium(II); "THF" means tetrahydrofuran; "C34H28FeP2.Cl2Pd" means [1,1'-bis(diphenylphosphino) ferrocene] dichloropalladium(ii); "i-PrOH" or "iPrOH" means 2-propanol; "LC" means liquid chromatography; "LCMS" means Liquid Chromatography/Mass spectrometry; "HPLC" means high-performance liquid chromatography; "int." means intermediate; "prep-HPLC" means preparative high-performance liquid chromatography; "m-CPBA" means meta-Chloroperoxybenzoic acid; "TFA" means trifluoroacetic acid; "m.p." means melting point; "RP" means reversed phase; "min" means minute(s); "h" means hour(s); "PE" means petroleum ether; "v/v" means volume per volume; "Celite®" means diatomaceous earth; "DMSO" means dimethyl sulfoxide; "SFC" means Supercritical Fluid Chromatography; "DIPE" means diisopropyl ether; "dppf" or "DPPF" means 1,1'-Bis(diphenylphosphino)ferrocene; "DIPEA" or "DIEA" means N,N-diisopropylethylamine; "PPh3" means triphenylphosphine; "Et2O" means diethyl ether; "Pd/C" means palladium on carbon; "Pt/C" means platina on carbon; "Pd(OH)2/C" means palladium hydroxide on carbon; "CPME" means cyclopentyl methyl ether; "Pd2(dba)3 means Tris(dibenzylideneacetone) dipalladium; "DIAD" means diisopropyl azodicarboxylate; "TMSCF3" means trimethyl(trifluoromethyl)silane; "TBAF" means tetrabutylammonium fluoride; "psi" means pound-force per square inch; "Et4NCl" means tetraethylammonium chloride; "eq." means equivalent(s); "Pd(OAc)2" means palladium(II) acetate; "AcOH" means acetic acid; "DMAP" means 4-(dimethylamino)pyridine; "t-BuOK", "tBuOK" or "KOtBu"means potassium tert-butoxide; "Dess-Martin periodinane" means 1,1,1-Triacetoxy-1,1-dihydro-1,2-benziodoxol-3(1H)-one; "TBDMSCl" means tert-Butyldimethylsilyl chloride; "PPh3-polymer" or "PPh3-pol" means triphenylphosphine polymer bound; "Ph3PCH3Br" means methyltriphenylphosphonium bromide; "Bn" means benzyl; "Bz" means benzoyl; "p-TSA" means 4-methylbenzenesulfonic acid; "BF3.Et2O" means Boron Trifluoride-Ethyl Ether Complex; "9-BBN" means 9-Borabicyclo[3.3.1]nonane; "Pd-118" means Dichloro[1,1'-bis(di-tert-butylphosphino)ferrocene]palladium(II); and "TLC" means thin layer chromatography; "prep-TLC" means preparative TLC;

"p-MeC6H4SO3H.H2O" means para toluenesulfonic acid hydrate; "PMB" means para methoxybenzyl; "KOAc" means potassium acetate; "PTSA" para toluenesulfonic acid; "MTBE" means methyl tert. butyl ether; Rh(acac)(eth) 2" means Acetylacetonatobis(ethylene)rhodium(I); "(S)-MonoPhos" means (S)-N,N-dimethyldinaphtho[2,1-D:1',2'-F][1,3,2]dioxaphosphepin-4-amine; "Tf2O" means triflic anhydride; "MeI" means methyliodide; "Me2NH" means dimethylamine; "Me2NH.HCl" means dimethylamine hydrochloric acid; "Me4NCl" means tetramethylammonium chloride; "MeONa" means sodium methoxide; "Ts" means tosyl; "MsCl" means mesylchloride; "DIBAH" means Diisobutylaluminium hydride;

"TBDMS" means tertButyl dimethylsilyl; "Pd(dppf) Cl2.CH2Cl2" means [1,1'-Bis(diphenylphosphino)ferrocene]dichloropalladium(II), complex with dichloromethane,; "PPA" means polyphosphoric acid;"NH2Bn" means benzylamine; "Pd(PPh3)2Cl2" means Dichlorobis(triphenylphosphine)palladium(II).

For intermediates that were used in a next reaction step as a crude or as a partially purified intermediate, estimated mol amounts (in some cases indicated by ≈) are indicated in the reaction protocols described below, or alternatively theoretical mol amounts are indicated.

Preparation of Intermediate 1

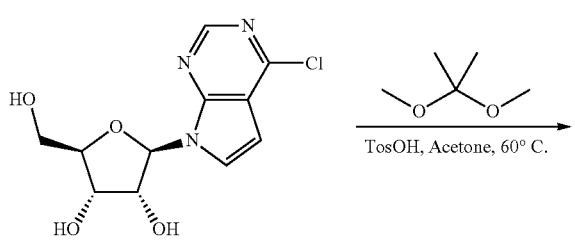

Preparation of Intermediate 59

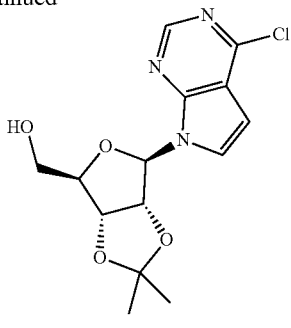

intermediate 1

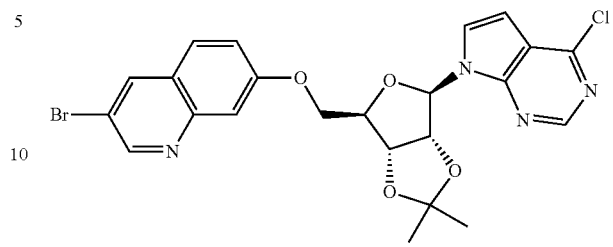

To a mixture of 6-chloro-7-deazapurinebeta-d-riboside (25.0 g, 87.5 mmol) in acetone (330 mL) was added 2,2-dimethoxypropane (18.2 g, 175 mmol) and 4-methylbenzenesulfonic acid (TosOH) (1.51 g, 8.75 mmol) in one portion at 25° C. under N2. The mixture was stirred at 60° C. for 2 hours. The mixture was cooled to 25° C. The reaction was quenched by adding saturated NaHCO3 (100 mL) slowly and then extracted with ethyl acetate (125 mL×5). The combined organic phase was washed with saturated brine (120 mL), dried with anhydrous MgSO4, filtered and concentrated in vacuum. The residue was purified by silica gel chromatography (gradient elution: DCM/Ethyl acetate from 1:0 to 2:1) to afford crude intermediate 1 (38.0 g) as light yellow gum.

Diisopropyl azodicarboxylate (0.221 mL, 1.125 mmol) was added dropwise to a stirred suspension of intermediate 1 (0.27 g, 0.80 mmol), 3-bromoquinolin-7-ol (0.18 g, 0.80 mmol) and triphenylphosphine resin (0.375 g, 3 mmol/g, 1.125 mmol) in THF (8 ml) at room temperature. After addition the reaction mixture was stirred for 18 hours. The reaction mixture was filtered over a pad of Dicalite®. The residue was washed with methanol. The solvents of the filtrate were evaporated. The residue was used as such in the next step.

Preparation of Intermediate 105

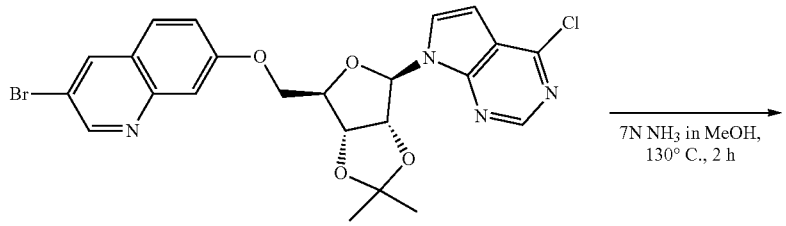

intermediate 59

7N NH3 in MeOH, 130° C., 2 h

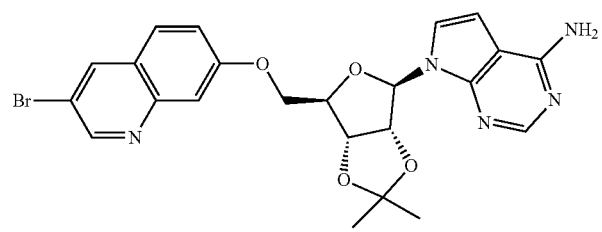

intermediate 105

The crude Intermediate 59 (q.s., theoretically 0.83 mmol) was dissolved in 7M NH3 in MeOH (20 mL, 7 M, 140 mmol). The resulting solution was stirred and heated at 130° C. using microwave irradiation for 2 hours. The solvents were evaporated. The residue was dissolved in dichloromethane and purified over a SiO2 column, type Grace Reveleris SRC, 12 g, Si 40, on a Grace Reveleris X2 purification system using dichloromethane and methanol as eluens in a gradient starting from 100% DCM for 20 column volumes to 20% MeOH and 80% DCM over 20 column volumes. The fractions containing the product were combined and the solvents were evaporated yielding crude Intermediate 105 (175 mg) used as such in the next reaction step.

Preparation of Compound 2

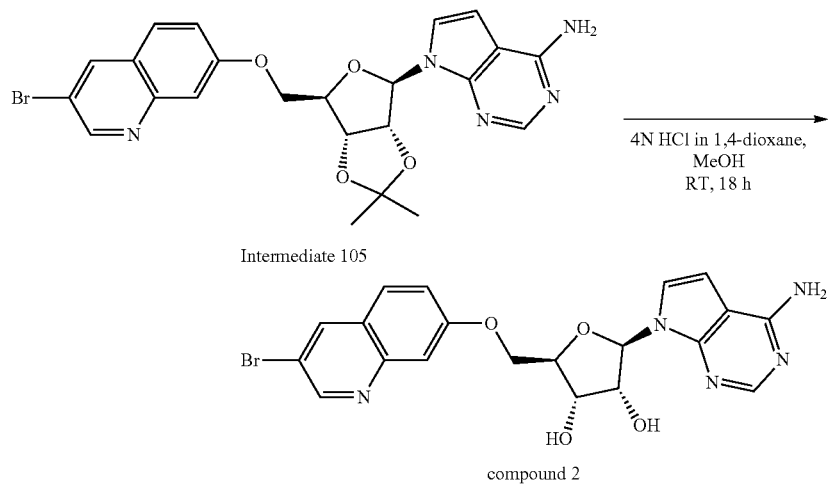

4M HCl in dioxane (0.7 mL, 2.9 mmol) was added to a stirred solution of intermediate 105 (175.1 mg, crude, ≈0.29 mmol) in MeOH (10 mL) at room temperature. The reaction mixture was stirred at room temperature for 18 hours. The reaction was quenched by the addition of 1.5 mL of a 7 N solution of NH3 in MeOH. The solvents were evaporated. The residue was dissolved in DCM. The precipitate was filtered off. The filtrate was purified over a SiO2 column, type Grace Reveleris SRC, 12 g, Si 40, on an Armen Spot II Ultimate purification system using DCM and MeOH as eluens in a gradient starting from 100% DCM and ending with 40% MeOH and 60% DCM. The fractions containing the product were combined and the solvents were evaporated yielding 24.5 mg of compound 2.

Preparation of Intermediate 10

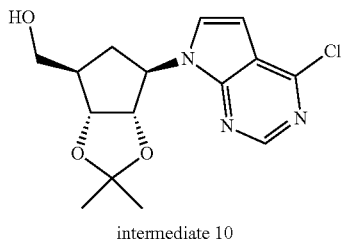 [SMILES: CC1(C)O[C@@H]2[C@@H](CO)C[C@@H](n3ccc4c(Cl)ncnc43)[C@@H]2O1]

intermediate 10

Step a)

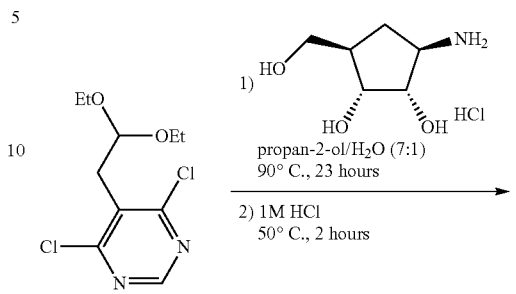

-continued

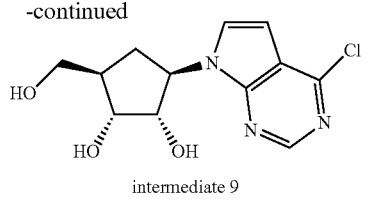

intermediate 9

To a mixture of 4,6-dichloro-5-(2,2-diethoxyethyl)pyrimidine (14.0 g, 52.8 mmol) and (1R,2S,3R,5R)-3-amino-5-(hydroxymethyl)cyclopentane-1,2-diol hydrochloride (10.7 g, 58.1 mmol) in propan-2-ol/H2O (208 mL, 7:1), was added Et3N (13.4 g, 132 mmol) in one portion at 25° C. under N2. The mixture was stirred at 90° C. for 23 hours. The mixture was cooled to 50° C. and 4M HCl (24 mL, 106 mmol) was added slowly. The residue was then stirred at 50° C. for 2 hours. The reaction mixture was cooled to 25° C. and NaHCO3 (14 g, 100 mmol) was added slowly. Ethyl acetate (230 mL) was added, followed by the addition of a half-saturated NaHCO3 solution (q.s.). The organic phase was isolated and the aqueous phase was extracted with ethyl acetate (230 mL×2). The combined organic phase was dried with anhydrous MgSO4, filtered and concentrated in vacuum to afford intermediate 9 as yellow solid (17.4 g, quantitative yield in 2 steps). The crude product was directly used as such in the next reaction step without further purification.

Step b)

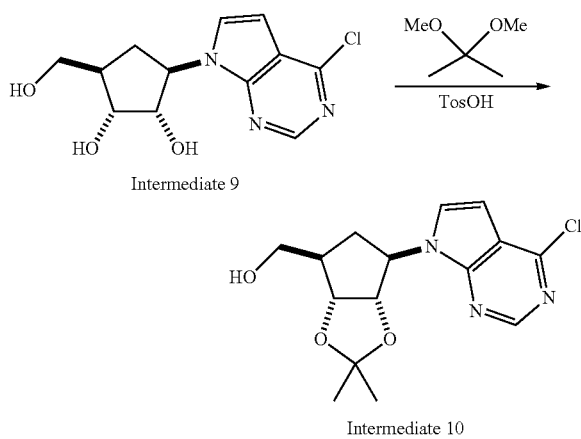

Intermediate 9

Intermediate 10

To a mixture of intermediate 9 (17.4 g, ≈52.7 mmol) in acetone (250 mL) was added 2,2-dimethoxypropane (11.0 g, 105 mmol) and TsOH.H2O (908 mg, 5.27 mmol) in one portion at 25° C. under N2. The mixture was stirred at 60° C. for 2 hours. The mixture was cooled to 25° C. and the solution was concentrated in vacuum, quenched by saturated NaHCO3 (100 mL) slowly and then extracted with ethyl acetate (100 mL×3). The combined organic phase was washed with saturated brine (100 mL), dried with anhydrous MgSO4, filtered and concentrated in vacuum. The residue was purified by flash chromatography on silica gel (gradient elution: DCM/Ethyl acetate from 1/0 to 2/1) to afford intermediate 10 as light yellow gum (15.5 g, 89% yield).

Preparation of Intermediate 33

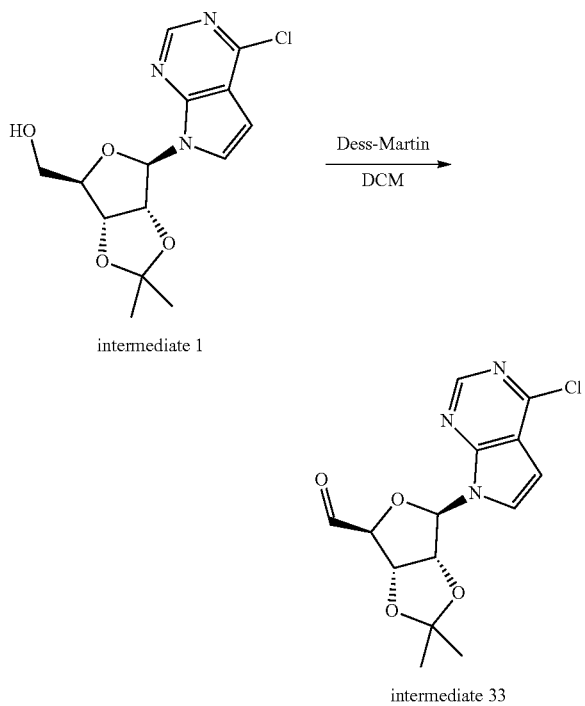

intermediate 1 intermediate 33

To a mixture of intermediate 1 (2.00 g, theoretically 6.18 mmol) in DCM (40 mL) was added Dess-Martin periodinane (5.24 g, 12.36 mmol) in one portion at 0° C. under N2. The mixture was stirred at 0° C. for 3 hours. To the mixture was added Na2S2O3 (4 g) in saturated NaHCO3 (20 mL) and stirred for 10 min. The aqueous phase was extracted with DCM (20 mL×3). The combined organic phase was washed with saturated brine (20 mL×2), dried with anhydrous MgSO4, filtered and concentrated in vacuum to afford intermediate 33 (1.80 g, crude) as light yellow gum. The crude product was directly used for the next reaction step without further purification.

Below intermediates were prepared by an analogous reaction protocol as was used for the preparation of intermediate 33 using the appropriate starting materials (Table 7).

TABLE 7

| Int. | structure | Starting material |
|---|---|---|
| 35 | 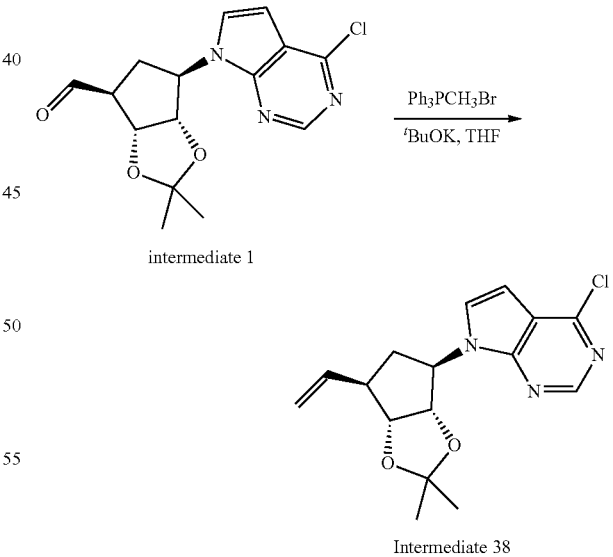 | intermediate 10 |

Preparation of Intermediate 38

Method 1 intermediate 1

Intermediate 38

To a mixture of methyltriphenylphosphonium bromide (4.87 g, 13.62 mmol) in THF (500 mL) was added t-BuOK (11.4 mL, 1 M in THF, 1.27 g, 11.35 mmol,) dropwise at 0° C. under N2. The suspension was turned to bright yellow and stirred at 0° C. for 0.5 h and then warmed to 25° C. for 0.5 h. The mixture was cooled to −40° C. The solution of Intermediate 35 (1.46 g, theoretically 4.54 mmol) in THF (130.0 mL) was added drop-wise and then stirred at −20° C. for 1 h, after this, the mixture was warmed to 25° C. for 2 h. To the mixture was added saturated NH4Cl (300 ml) and stirred for 10 min. Layers were separated and the aqueous phase was extracted with DCM (300 mL×2). The combined organic phase was washed with saturated brine (500 mL), dried with anhydrous MgSO4, filtered and concentrated in vacuum. The residue was purified by silica gel chromatography (ISCO®; 80 g SepaFlash® Silica Flash Column, Gradient eluention: From 0 to 15% of Ethyl acetate/Petroleum ether). The desired fractions were collected and the solvent was evaporated. Intermediate 38 was obtained as off-white solid (530 mg, 36% yield).

Method 2

Intermediate 38

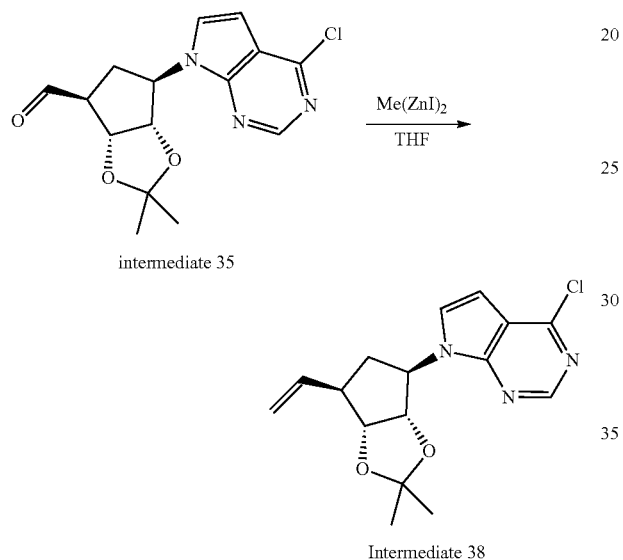

intermediate 35

Intermediate 38

A solution of Intermediate 35 (10.0 g, theoretically 31.1 mmol) in THF (100 mL) was added drop-wise under N2 over a period of 30 minutes to a bis(iodozincio)methane solution in THF (180 mL, 0.31 M, 55.9 mmol, prepared according to the procedure described in Tetrahedron 2002, 58, 8255-8262), stirring was continued until complete conversion (approximately 2 hours). The reaction mixture was quenched by the slow addition of a saturated aqueous NH4Cl solution, during which salt formation was observed. Prior to extraction (EtOAc, 2×200 mL), the salts were dissolved again by the addition of an aqueous ammonia solution (25%). The combined organic phases were washed with an aqueous sodium bisulfite solution and brine, dried with anhydrous MgSO4, filtered and concentrated in vacuum. The residue was purified by silica gel chromatography (eluent: dichloromethane/EtOAc 95/5) to provide Intermediate 38 as an off-white solid (6.9 g, 66%).

Preparation of Intermediate 174

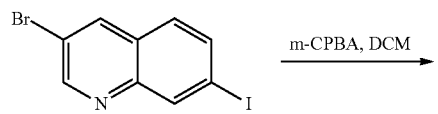

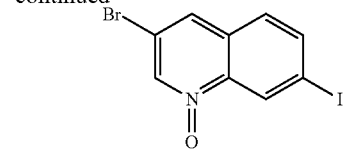

intermediate 174

3-Bromo-7-iodo-quinoline (5.99 g, 17.7 mmol) was dissolved in dichloromethane (60 mL), then m-CPBA (4.57 g, 26.5 mmol) was added in portions. The mixture was stirred at room temperature for 4 days. The mixture was quenched by a saturated Na2S2O3 aqueous solution (40 mL) and a saturated NaHCO3 aqueous solution (PH to 6-7), then extracted by dichloromethane (50 mL×3). The organic phase was washed with H2O (50 mL), dried with anhydrous Na2SO4 and evaporated under reduced pressure. The residue was purified by silica gel column (eluent: petroleum ether/ethyl acetate=10/1 to 1/1) to afford the desired product intermediate 174 (1.9 g, 14.1% yield) as a yellow solid.

Preparation of Intermediate 175

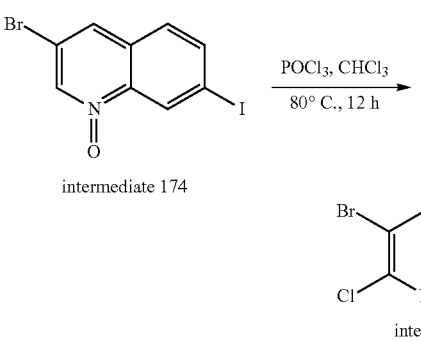

intermediate 174 intermediate 175

To a solution of intermediate 174 (2.9 g, 8.29 mmol) in chloroform (60 mL) was added phosphoryl trichloride (8.3 g, 54.1 mmol). The mixture was stirred at 80° C. for 12 h. The mixture was evaporated under reduced pressure to obtain crude product. The crude product was purified by chromatography column (eluent: petroleum ether/ethyl acetate=10/1 to 1/1). The desired fractions were collected and concentrated to give product intermediate 175 (1.3 g, 41.5% yield) as a white solid.

Preparation of Intermediate 176

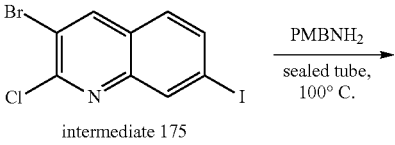

intermediate 175 intermediate 176

4-methoxybenzylamine (1.34 g, 9.78 mmol) was added into the mixture of intermediate 175 (0.8 g, ≈21.95 mmol) in ethanol (10 ml). The mixture was heated in a sealed tube at 100° C. for 12 h. The mixture was evaporated under vacuo to obtain the crude product. This was purified by chromatography column (gradient eluent: ethyl acetate/petroleum ether from 0/1 to 1/10). The desired fractions were collected and concentrated to give product intermediate 176 (600 mg, 51.6% yield) as an oil.

Preparation of Intermediate 177

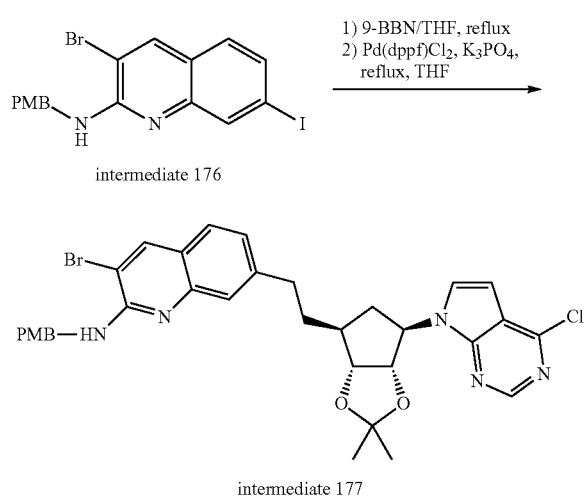

intermediate 176 intermediate 177

A mixture of intermediate 38 (44 mg, 0.138 mmol) in 9-BBN (1.3 ml, 0.69 mmol, 0.5M in THF) was refluxed for 1 h under N2. The mixture was cooled to room temperature, then K3PO4 (87 mg, 0.413 mmol) in H2O (1 mL) was added, followed by THF (5 ml), intermediate 176 (122.727 mg, 20.206 mmol) and [1,1'-bis(diphenylphosphino)ferrocene]dichloropalladium(II) (4.48 mg, 0.007 mmol). The reaction mixture was refluxed for 3 hours. The mixture was concentrated. The residue was dissolved in ethyl acetate (40 ml), washed with water (6 ml), brine (6 ml).The organic phase was dried over Na2SO4, filtered and concentrated to give crude intermediate 177 fraction 1 (120 mg, 71.5% yield).

A mixture of intermediate 38 (233.7 mg, 0.73 mmol) in 9-BBN (7.31 ml, 3.65 mmol, 0.5M in THF) was refluxed for 1 h under N2. The mixture was cooled to room temperature, then K3PO4 (87 mg, 0.413 mmol) in H2 O (1 mL) was added, followed by THF (5 ml), intermediate 176 (478 mg, ≈20.80 mmol) and [1,1'-bis(diphenylphosphino)ferrocene] dichloropalladium(II)(23.8 mg, 0.037 mmol). The reaction mixture was refluxed for 3 hours. The mixture was concentrated. The residue was dissolved in ethyl acetate (40 ml), washed with water (6 ml), brine (6 ml). The organic phase was dried over Na2SO4, filtered and concentrated to with crude intermediate 177 fraction 2 (600 mg, 63.1% yield).

The two fractions were combined and purified by chromatography column (gradient eluent: ethyl acetate/petroleum ether from 1/10 to 1/1). The desired fractions were collected and concentrated to give intermediate 177 (300 mg, 61.0% yield) as a solid.

Preparation of Intermediate 178

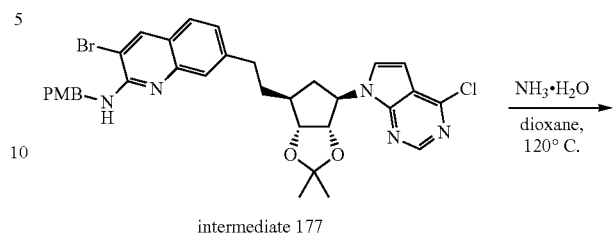

intermediate 177

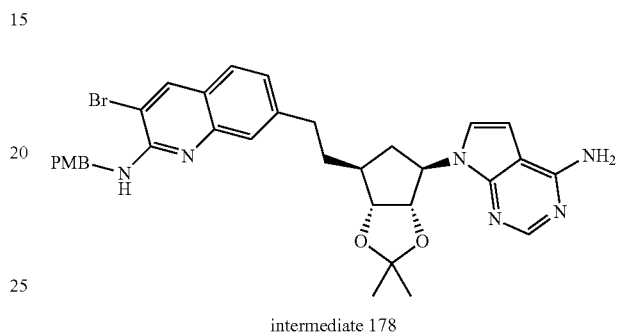

intermediate 178

A mixture of intermediate 177 (300 mg, 0.446 mmol) and NH3.H2O (10 ml) in dioxane (10 ml) was stirred in a sealed tube at 120° C. for 14 h. This reaction was evaporated under vacuo to obtain intermediate 178 (250 mg, 87.1% yield) as an oil.

Preparation of intermediate 179

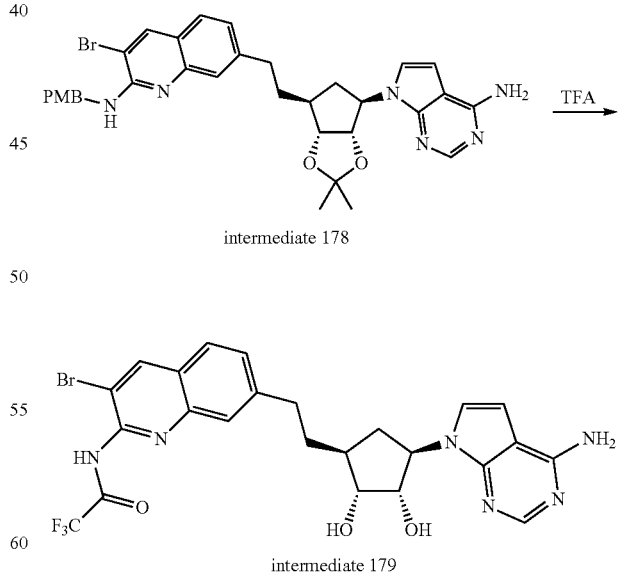

intermediate 178 intermediate 179

The mixture of intermediate 178 (250 mg, 0.388 mmol) in TFA (5 ml) was stirred at 50° C. for 1 h. The mixture was evaporated under vacuo to obtain intermediate 179 (350 mg, 63.4% yield) as an oil.

Preparation of Compound 80

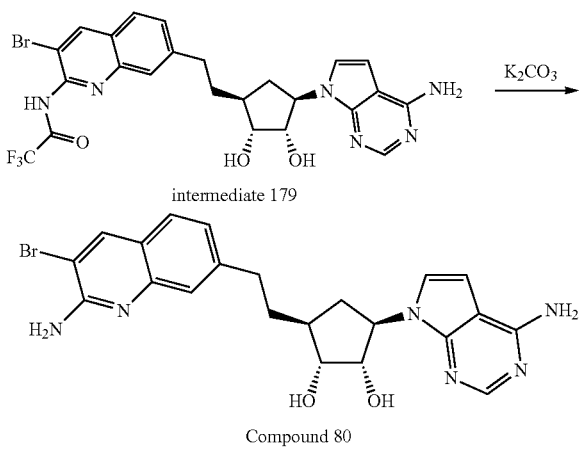

intermediate 179

Compound 80

The mixture of intermediate 179 (350 mg) and K2CO3 (102 mg, 0.74 mmol) in methanol (3 mL) was stirred at 60° C. for 1 h. The mixture was filtered and evaporated under vacuo to obtain a crude product. The crude product was purified by prep-HPLC (Column: Waters Xbridge Prep OBD C18 150×30 mm, 5 μm, Condition: gradient water (0.05% ammonia hydroxide v/v)-ACN). The desired fractions were collected and the solvent was evaporated to give Compound 80 (113.3 mg, 94.9% yield) as a white solid.

Analytical Part

NMR

For a number of compounds, 1H NMR spectra were recorded on a Bruker DPX-360 operating at 360 MHz, on a Bruker Avance 600 operating at 600 MHz, on a Bruker Avance 400 operating at 400 MHz, or on a Varian 400MR spectrometer operating at 400 MHz. As solvents CHLOROFORM-d (deuterated chloroform, CDCl3), Methanol-d4 or DMSO-d6 (deuterated DMSO, dimethyl-d6 sulfoxide) were used. Chemical shifts (δ) are reported in parts per million (ppm) relative to tetramethylsilane (TMS), which was used as internal standard.

Co. 80: $^1$H NMR (600 MHz, DMSO-$d_6$) δ ppm 1.50-1.56 (m, 1 H) 1.68-1.75 (m, 1 H) 1.85-1.92 (m, 1 H) 1.96 (ddt, J=13.0, 9.0, 6.5, 6.5 Hz, 1 H) 2.25 (dt, J=12.7, 7.9 Hz, 1 H) 2.69-2.80 (m, 2 H) 3.76 (br t, J=4.7 Hz, 1 H) 4.21 (dd, J=7.6, 6.0 Hz, 1 H) 4.57 (br s, 1 H) 4.72 (br s, 1 H) 4.80 (dt, J=10.5, 7.9 Hz, 1 H) 6.50 (br s, 2 H) 6.59 (d, J=3.5 Hz, 1 H) 7.07 (br s, 2 H) 7.12 (dd, J=8.2, 1.6 Hz, 1 H) 7.29 (d, J=3.6 Hz, 1 H) 7.34 (s, 1 H) 7.58 (d, J=8.1 Hz, 1 H) 8.07 (s, 1 H) 8.31 (s, 1 H).

Experimental Procedures in Vitro Assay (Assay 1a and 1b)

Reagents

PRMT5-MEP50 enzyme was purchased from Charles River (Argenta). The enzyme complex was produced in insect cells (Sf9) infected simultaneously with two baculoviruses. One virus expresses full length human PRMT5 with Flag-tag at N-terminus, the second virus expresses full length MEP50 with His6-TEV cleavage at N-terminus. The protein was affinity purified using anti-Flag (M2) beads eluted with 3×FLAG peptide, followed by His-Select eluted with 0.5M imidazole. Eluted protein was then dialysed against tris-buffered saline (TBS) (pH 8.0) containing 20% glycerol and 3 mM dithiothreitol (DTT).

Full-length untagged human recombinant histone H2A (residues 1-130, Genbank Accession #NM_021052, MW=14.1 kDa) expressed in *E. coli* was purchased from Reaction Biology Corporation, Cat #HMT-11-146. Reagents used for making reaction buffer or stopping reaction were purchased including Tris base (Sigma Cat #T-1503), NaCl (Sigma Cat #RGF-3270), MgCl2 (Sigma Cat #M0250), DTT (Invitrogen Cat #15508-013) and Formic Acid (Riedel deHaen, Cat #33015)

High Throughput Mass Spectrometer Assay

PRMT5 catalyzes the sequential methylations of the terminal nitrogen atoms on the guanidine groups of arginine residues within proteins using co-substrate S-adenosyl-L-methionine (AdoMet, SAM), forming mono-methyl (MMA), symmetric-dimethyl arginine (sDMA) and S-adenosyl-L-homocysteine (AdoHcy, SAH). The enzyme activity was determined by following the product SAH formation using high throughput mass spectrometry (Agilent Rapidfire 300 System coupled to a Sciex 4000 series QTrap® triple-quad MS/MS). The reaction buffer was 20 mM Tris-HCl, pH 8.5, 50 mM NaCl, 5 mM MgCl2 and 1 mM DTT. The reaction activity was stopped using 1% formic acid (final concentration).

Inhibition Studies. The IC50 Studies were performed using eleven point dosing series made for each compound by serially diluted 1:2 in dimethyl sulfoxide (DMSO), with point 12 being a DMSO control. Compounds were first spotted to plates, and followed by addition of 2 μM SAM and 0.6 μM H2A (histone H2A) solution mixture. The same volume of enzyme solution was added to initiate the enzymatic reactions. The final concentrations of the reaction are at 1 μM SAM, 0.3 H2A and 10 nM enzyme (assay 1a) or or 1.25 nM enzyme (assay 1b). The reaction was incubated at 30° C. for 60 minutes (min) when 10 nM enzyme was used and for 120 min when 1.25 nM enzyme was used. Subsequently, the reaction was quenched by addition of formic acid to a final concentration of 1%. The inhibitions of SAH formation in the presence of compounds were calculated as a percentage of the control relative to the uninhibited reaction as a function of inhibitor concentration. The data were fit as follows:

$$Y = \text{Bottom} + (\text{Top} - \text{Bottom})/(1 + 10^{((\log \text{IC50} - X)*h)})$$

where IC50 is the inhibitor concentration (same unit as X) at 50% inhibition and h is the Hill slope. Y is percent of inhibition, X is log of compound concentration. Bottom and Top are the plateaus in same units as Y.

The pIC50 values in Table 1 below are averaged values (Co. No. means compound number).

TABLE 1

| Co. No. | pIC$_{50}$ Assay 1a | pIC$_{50}$ Assay 1b |
|---|---|---|
| 2 | 8.1 | 7.6 |
| 80 | 9.9 | 9.7 |

Example 1

PIK3CA Activating Mutations are Associated with PRMT5 Inhibitor Sensitivity in SCLC The cellular sensitivity profile of compound 2 was assessed in the SCLC sub-classification of a broad lung cancer cell line panel. Strikingly, some of the most sensitive cell lines harbor different gain-of-function mutations in the PIK3Cα gene, and are mentioned in Table 2. Activation of the PI3Kα pathway (gain-of-function mutations or pathway stimulation) as a tumor response towards standard-of-care (cisplatin) or even towards targeted agents like the latest PARP inhibitor generation, implicates a crucial role in the process of resistance that might be linked with low overall survival of SCLC patient post-therapy.

TABLE 2

| Cell line | PIK3CA mutation | Histology subtype | GI50 |
| --- | --- | --- | --- |
| NCI-H1048 | H1047R | SCLC | 94.62 nM |
| LU99a | T1025A | SCLC | 128.53 nM |
| H69V | G106_R108del | SCLC | 85.62 nM |

Example 2

Spliceosome Alterations are Associated with PRMT5 Inhibitor-Sensitivity in NSCLC Cancer-specific splicing events are known to initiate malignancy and also contribute to disease progression. So far, two proteins involved in splicing, U2AF1 and RBM10, have been described to be miss-regulated in NSCLC.

U2AF1, a well characterized splicing factor, harbors a gain-of-function hot-spot mutation (S34F) in 3-8% of NSCLC patients. Recently, the RNA binding protein RBM10, also crucial for the assembly of the spliceosome, has been classified as a tumor suppressor that is inactivated by loss-of-function mutations, predominantly in NSCLC patients (~8%) with a smoking history.

Sm proteins, crucial for spliceosome assembly, have been described as direct substrates of PRMT5 and therefore, PRMT5 function has been linked to modulate spliceosome activity.

Since the S34F gain-of-function mutation in U2AF1 has been confirmed as oncogenic, a small panel of all commercial available NSCLC cell lines, harboring the S34F mutation, was assembled to analyze the potential synthetic lethal relation between U2AF1-S34F and PRMT5 inhibition.

All (three out of three) NSCLC cells that harbor this hot-spot mutation are proliferation sensitive to the PRMT5 inhibitor compound 2, see Table 3.

TABLE 3

| Cell line | Gene/mutation | Histology subtype | GI50 |
| --- | --- | --- | --- |
| NCI-H441 | U2AF1-S34F | Adenocarcinoma | 98.40 nM |
| LC-2/ad | U2AF1-S34F | Adenocarcinoma | 116.08 nM |
| HCC78 | U2AF1-S34F | Adenocarcinoma | 107.65 nM |

Example 3

Cyclin D1 Pathway Amplifications are Associated with PRMT5 Inhibitor-Sensitivity in NSCLC Amplification and/or increased expression of the G1 cyclin family has been reported in multiple cancers, including NSCLC. A correlation has been observed between PRMT5 and the expression of modulators of the cell cycle, including Cyclin D1, CDK4 and CDK6, suggesting that PRMT5 may have a regulatory effect on the G1 phase. Analysis of the compound 2-treated lung cell line panel revealed a significant association between Cyclin D1/CDK4/CDK6 amplification(s) and PRMT5i-sensitivity, indicating that cyclin pathway aberrations can be used as markers for patient selection. Table 4 shows that NSCLC cell lines harbouring such Cyclin D1/CDK4/CDK6 amplification(s) are sensitive to treatment with compound 2.

TABLE 4

| Cell line | Amplified gene | Histology subtype | GI50 |
| --- | --- | --- | --- |
| EPLC272H | Cyclin D1 | Adenocarcinoma | 98.53 nM |
| NCI-H226 | CDK4 | Adenocarcinoma | 204.52 nM |
| HLC1 | CDK6 | Squamous Cell Carcinoma | 96.39 nM |

Example 4

WNT Pathway Alterations are Associated with PRMT5 Inhibitor-Sensitivity

Cell lines harboring mutations in key Wnt signaling genes, including β-catenin and APC, show sensitivity to PRMT5i treatment as shown in table 5

TABLE 5

| Cell line | Gene/mutation | Histology subtype | GI50 |
| --- | --- | --- | --- |
| A427 | CTNNB1/T41A | Adenocarcinoma | 166.52 nM |
| HCC15 | CTNNB1/S45F, Y670* | Squamous Cell Carcinoma | 266.07 nM |
| LK2 | APC/W685*, E1020K | Squamous Cell Carcinoma | 114.53 nM |

EXAMPLES

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

The disclosures of each patent, patent application, and publication cited or described in this document are hereby incorporated herein by reference, in its entirety.

What is claimed:

1. A method of treating a non-small cell lung cancer (NSCLC) in a human patient, the method comprising:
administering a protein arginine N-methyltransferase 5 (PRMT5) inhibitor to the human patient, wherein the human patient has been determined to have a I696fs mutation in RBM10 wherein the PRMT5 inhibitor is

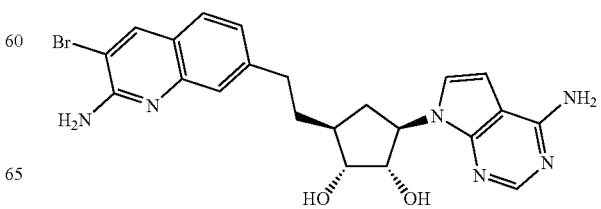

-continued
or

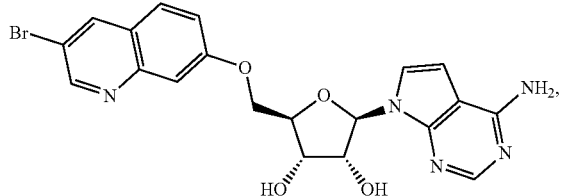

or a pharmaceutically acceptable salt thereof or a solvate thereof.

2. The method of claim 1, wherein the human patient has been determined to have the I696fs mutation in RBM10 by testing a biological sample from the human patient for the presence of the I696fs mutation in RBM10, and wherein the testing of the biological sample from the patient comprises:
isolating RNA from the biological sample;
synthesizing cDNA from the isolated RNA;
pre-amplifying the cDNA; and
amplifying the pre-amplified cDNA with a pair of primers that bind to and amplify the mutation.

3. The method of claim 1, wherein the PRMT5 inhibitor is

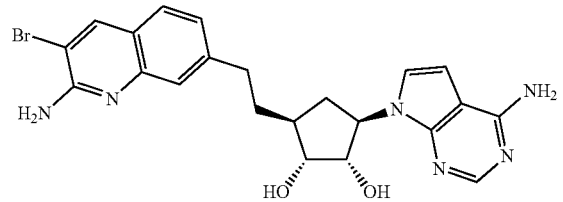 [SMILES: Nc1nc2cc(CC[C@H]3C[C@@H](n4ccc5c(N)ncnc54)[C@H](O)[C@@H]3O)ccc2cc1Br]

or a pharmaceutically acceptable salt thereof or a solvate thereof.

4. The method of claim 1, wherein the PRMT5 inhibitor is

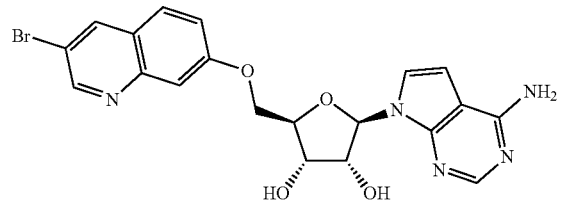 [SMILES: Nc1ncnc2c1ccn2[C@@H]1O[C@H](COc2ccc3cc(Br)cnc3c2)[C@@H](O)[C@H]1O]

or a pharmaceutically acceptable salt thereof or a solvate thereof.

5. A method of treating a human patient having a NSCLC with a protein arginine N-methyltransferase 5 (PRMT5) inhibitor, the method comprising:
testing a biological sample from the human patient having the NSCLC for the presence of a I696fs mutation in RBM10; and
administering the PRMT5 inhibitor to the human patient having the I696fs mutation, wherein the PRMT5 inhibitor is

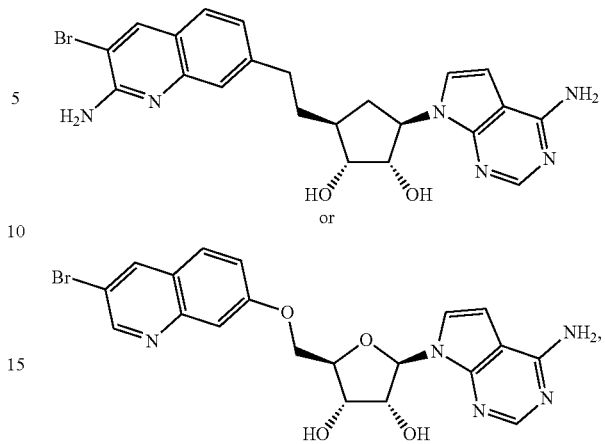

or a pharmaceutically acceptable salt thereof or a solvate thereof.

6. The method of claim 5, wherein the testing of the biological sample from the human patient comprises:
isolating RNA from the biological sample;
synthesizing cDNA from the isolated RNA;
pre-amplifying the cDNA; and
amplifying the pre-amplified cDNA with a pair of primers that bind to and amplify the mutation.

7. The method of claim 5, wherein the PRMT5 inhibitor is

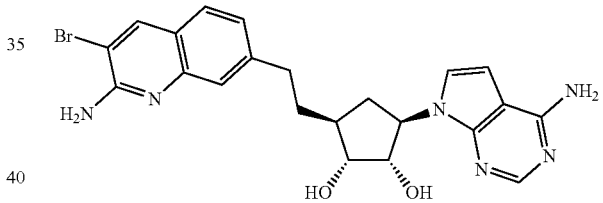

or a pharmaceutically acceptable salt thereof or a solvate thereof.

8. The method of claim 5, wherein the PRMT5 inhibitor is

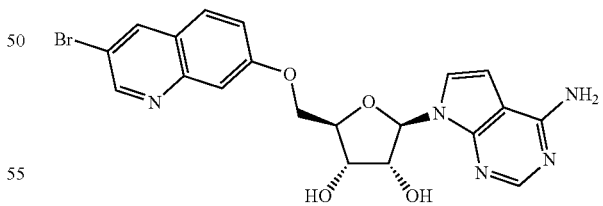

or a pharmaceutically acceptable salt thereof or a solvate thereof.

* * * * *